United States Patent
De Ridder

(10) Patent No.: US 8,463,387 B2
(45) Date of Patent: *Jun. 11, 2013

(54) STIMULATION OF THE AMYGDALOHIPPOCAMPAL COMPLEX TO TREAT NEUROLOGICAL CONDITIONS

(75) Inventor: Dirk De Ridder, Zelzate (BE)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/567,679

(22) Filed: Aug. 6, 2012

(65) Prior Publication Data

US 2013/0018435 A1   Jan. 17, 2013

Related U.S. Application Data

(63) Continuation of application No. 12/577,640, filed on Oct. 12, 2009, now Pat. No. 8,239,029, which is a continuation of application No. 11/254,612, filed on Oct. 20, 2005, now Pat. No. 7,603,174.

(60) Provisional application No. 60/620,847, filed on Oct. 21, 2004, provisional application No. 60/631,089, filed on Nov. 24, 2004, provisional application No. 60/639,365, filed on Dec. 27, 2004.

(51) Int. Cl.
*A61N 1/36* (2006.01)

(52) U.S. Cl.
USPC .......................................................... 607/45

(58) Field of Classification Search
None
See application file for complete search history.

(56) References Cited

U.S. PATENT DOCUMENTS

| | | | |
|---|---|---|---|
| 4,541,432 | A | 9/1985 | Molina-Negro et al. |
| 5,335,657 | A | 8/1994 | Terry, Jr. et al. |
| 5,496,369 | A | 3/1996 | Howard, III |
| 5,603,726 | A | 2/1997 | Schulman et al. |
| 5,697,975 | A | 12/1997 | Howard, III |
| 5,713,847 | A | 2/1998 | Howard, III et al. |
| 5,735,885 | A | 4/1998 | Howard, III et al. |
| 5,788,656 | A | 8/1998 | Mino |
| 5,938,690 | A | 8/1999 | Law et al. |
| 6,109,269 | A | 8/2000 | Rise et al. |
| 6,210,321 | B1 | 4/2001 | Di Mino et al. |
| 6,263,237 | B1 | 7/2001 | Rise |
| 6,295,472 | B1 | 9/2001 | Rubinstein et al. |
| 6,456,886 | B1 | 9/2002 | Howard, III et al. |

(Continued)

FOREIGN PATENT DOCUMENTS

| | | |
|---|---|---|
| EP | 0811395 | 12/1997 |
| EP | 1145735 | 10/2001 |

(Continued)

OTHER PUBLICATIONS

Barbas, et al., "Projections from the amygdala to basoventral and mediodorsal prefrontal regions in the rhesus monkey," J. Comp. Neurol., 300(4): 549-71, 1990.

(Continued)

*Primary Examiner* — Carl H Layno
*Assistant Examiner* — Paula J Stice

(57) ABSTRACT

A system and/or method treating for a neurological disorder by brain region stimulation. The system and/or method comprises a probe and a device to provide stimulation. The probe has a stimulation portion implanted in communication with a predetermined brain region site. The stimulation portion of the probe may be implanted in contact with a predetermined brain region.

6 Claims, 5 Drawing Sheets

U.S. PATENT DOCUMENTS

| | | | |
|---|---|---|---|
| 6,529,774 | B1 | 3/2003 | Greene et al. |
| 6,567,696 | B2 | 5/2003 | Voznesensky et al. |
| 6,581,046 | B1 | 6/2003 | Ahissar |
| 6,609,030 | B1 | 8/2003 | Rezai et al. |
| 6,609,031 | B1 | 8/2003 | Law et al. |
| 6,622,047 | B2 | 9/2003 | Barrett et al. |
| 6,656,172 | B1 | 12/2003 | Hildeband |
| 6,671,555 | B2 | 12/2003 | Gielen et al. |
| 6,690,974 | B2 | 2/2004 | Archer et al. |
| 6,721,603 | B2 | 4/2004 | Zabara et al. |
| 6,735,475 | B1 | 5/2004 | Whitehurst et al. |
| 6,740,072 | B2 | 5/2004 | Starkweather et al. |
| 6,748,276 | B1 | 6/2004 | Daignault, Jr. et al. |
| 7,603,174 | B2 | 10/2009 | DeRidder |
| 8,239,029 | B2 | 8/2012 | DeRidder |
| 2001/0029391 | A1 | 10/2001 | Gluckman et al. |
| 2001/0051819 | A1 | 12/2001 | Fischell et al. |
| 2002/0013612 | A1 | 1/2002 | Whitehurst |
| 2002/0151939 | A1 | 10/2002 | Rezai |
| 2003/0135248 | A1 | 7/2003 | Stypulkowski |
| 2003/0181954 | A1 | 9/2003 | Rezai |
| 2004/0133248 | A1 | 7/2004 | Frei et al. |
| 2004/0193231 | A1 | 9/2004 | David et al. |
| 2005/0043646 | A1 | 2/2005 | Viirre et al. |
| 2005/0070971 | A1 | 3/2005 | Fowler et al. |
| 2005/0143799 | A1 | 6/2005 | Black et al. |
| 2005/0143800 | A1 | 6/2005 | Lando et al. |

FOREIGN PATENT DOCUMENTS

| | | |
|---|---|---|
| WO | WO 0108617 | 2/2001 |
| WO | WO 03010540 | 2/2003 |
| WO | WO 2004045242 | 5/2004 |

OTHER PUBLICATIONS

Barbas, et al., Topographically Specific Hippocampal Projections Target Functionally Distinct Prefrontal Areas in the Rhesus Monkey, Hippocampus vol. 5, 1995, pp. 511-533.

Beurrier, et al., "Subthalamic nucleus neurons switch from single-spike activity to burst-firing mode," J. Neurosci., 19(2): 599-609, 1999.

Bremner, J.D., Structural Changes in the Brain in Depression and relationship to Symptom Recurrence, CNS Spectrums, vol. 7, No. 2, Feb. 2002, pp. 129-139.

Brown, et al., "Motor cortex stimulation for central and neuropathic pain: current status," Pain, 104(3): 431-435, 2003.

Brozoski, et al., "Elevated fusiform cell activity in the dorsal cochlear nucleus of chinchillas with psychophysical evidence of tinnitus," J. Neurosci., 22(6): 2383-90, 2002.

Bruehlmeier, et al., "How does the human brain deal with a spinal cord injury?" Eur. J. Neurosci., 10(12): 3918-22, 1998.

Brumberg, "Ionic mechanisms underlying repetitive high-frequency burst firing in supragranular cortical neurons," J. Neurosci., 20(13): 4829-4843, 2000.

Caetano, et al., "Anatomical MRI study of hippocampus and amygdala in patients with current and remitted major depression," Psychiatry Res., 132(2): 141-147, 2004.

Cazals, et al., "Alterations in average spectrum of cochleoneural activity by long-term salicylate treatment in the guinea pig: a plausible index of tinnitus," J. Neurophysiol., 80(4): 2113-20, 1998.

Chiry, Oriana, et al.; Patterns of calcium-binding proteins support parallel and hierarchical organization of human auditory areas; European Journal of Neuroscience, 17:397-410, 2003.

Condes-Lara, et al., "Brain somatic representation of phantom and intact limb: a fMRI study case report," Eur. J. Pain, 4(3): 239-45, 2000.

Coro, et al., "Receptor cell habituation in the A1 auditory receptor of four noctuoid moths," J. Exp. Biol., 201 (Pt 20): 2879-2890, 1998.

DelBello, et al., "Magnetic resonance imaging analysis of amygdala and other subcortical brain regions in adolescents with bipolar disorder," Bipolar Disord., 6(1): 43-52, 2004.

DeRidder, Dirk, et al.; Magnetic and electrical stimulation of the auditory cortex for intractable tinnitus: J. Neurosurg, 100:560-564, 2004.

Diamond, et al., "Preclinical Research on Stress, Memory and the Brain in the Development of Pharmacotherapy for Depression," European Neuropsychopharmacology vol. 14, 2004, pp. S491-S495.

Disney, et al., "Neurosteroids mediate habituation and tonic inhibition in the auditory midbrain," J. Neurophysiol., 86(2): 1052-6, 2001.

Doetsch, et al., "Short-term plasticity in primary somatosensory cortex of the rat: rapid changes in magnitudes and latencies of neuronal responses following digit denervation," Exp. Brain Res., 112: 505-512, 1996.

Drevets, et al., "Functional Anatomical Correlates of Antidepressants Drug Treatment Assessed Using PET Measures of Regional Glucose Metabolism," European Neuropsychopharmacology vol. 12, 2002, pp. 527-544.

Edline, et al., "Auditory thalamus neurons during sleep: changes in frequency selectivity, threshold, and receptive field size," J. Neurophysiol., 84(2): 934-52, 2000.

Eichhammer, Peter, et al.; Brief Report: Neuronavigated Repetitive Transcranial Magnetic Stimulatin in Patients with Tinnitus: A short Case Series; Biol. Psychiatry, 54:862-865, 2003.

Flor, "Cortical reorganisation and chronic pain: implications for rehabilitation," J. Rehabil. Med., (41 Suppl): 66-72, 2003.

Flor, et al., "Phantom-limb pain as a perceptual correlate of cortical reorganization following arm amputation," Nature, 375(6531): 482-484, 1995.

Fossati, et al., "Neuroplasticity: from MRI to depressive Symptoms," European Neuropsychophamacology vol. 14, 2004, pp. S503-S510.

Foxe, et al., "Multisensory auditory-somatosensory interactions in early cortical processing revealed by high-density electrical mapping," Cognitive Brain Research, 10: 77-83, 2000.

Foxe, John J., et al.; Auditory-Somatosensory Multisensory Processing in Auditory Association Cortex: An fMRI Study; J. Neurophysiol., 88:540-543, 2002.

Fu, et al., "Auditory cortical neurons respond to somatosensory stimulation," J. Neuroscience, 23(20): 7510-7515, 2003.

Givois, et al., "Sensory habituation of auditory receptor neurons: implications for sound localization," J. Exp. Biol., 203 (Pt 17): 2529-37, 2000.

Halbert, et al., "Evidence for the optimal management of acute and chronic phantom pain: a systematic review," Clin. J. Pain, 18(2): 84-92, 2002.

Haldane, et al., "New Insights Help Define the Pathophysiology of Bipolar Affective Disorder: Neuroimaging and Neuropathology Findings," Progress in Neuro-Psychopharmacology & Biological Psychiatry vol. 28, 2004, pp. 943-960.

He, "Modulatory effects of regional cortical activation on the onset responses of the cat medial geniculate neurons," J. Neurophysiol., 77(2): 896-908, 1997.

He, et al., "Differential distribution of burst and single-spike responses in auditory thalamus," J. Neurophysiol., 88(4): 2152-6, 2002.

He, et al., "Modulatory effect of cortical activation on the lemniscal auditory thalamus of the Guinea pig," J. Neurophysiol., 88(2): 1040-50, 2002.

Hilty, et al., "A Review of Bipolar Disorder Among Adults," Psychiatric Services vol. 50, 1999, pp. 201-213.

Howard III, "Tinnitus and Auditory Cortex," J. Neurosurg., 101: 171-172, 2004.

Huang, et al., "Theta burst stimulation of the human motor cortex," Neuron, 45(2): 201-6, 2005.

Huerta, et al., "Low-frequency stimulation at the troughs of theta-oscillation induces long-term depression of previously potentiated CA1 synapses," J. Neurophysiol., 75(2): 877-84, 1996.

Jastreboff, et al., "Phantom auditory perception (tinnitus): mechanisms of generation and perception," Neurosci. Res., 8(4): 221-54, 1990.

Javitt, et al., "Role of cortical N-methyl-D-aspartate receptors in auditory sensory memory and mismatch negativity generation: implications for schizophrenia," Proc. Natl. Acad. Sci. USA, 93(21): 11962-7, 1996.

Joliot, et al., "Human oscillatory brain activity near 40 Hz coexists with cognitive temporal binding," Proc. Natl. Acad. Sci. USA, 91(24): 11748-51, 1994.

Jones, "The thalamic matrix and thalamocortical synchrony," Trends in Neuroscience, 24(10): 595-601, 2001.

Kaas, et al., "The reorganization of somatosensory cortex following peripheral nerve damage in adult and developing mammals," Annu. Rev. Neurosci., 6: 325-56, 1983.

Kandel, "Cellular mechanisms of hearing and the biological basis of individuality," Principles of Neural Science, 3rd ed. Appleton & Lange Norwalk, Connecticut: 1009-1031, 1991.

Katayama, et al., "Motor cortex stimulation for phantom limb pain: comprehensive therapy with spinal cord and thalamic stimulation," Stereotact. Funct. Neurosurg., 77(1-4): 159-62, 2001.

Kepecs, et al., "Bursting neurons signal input slope," J. Neurosci., 22(20): 9053-62, 2002.

Knecht, et al., "Plasticity of plasticity? Changes in the pattern of perceptual correlates of reorganization after amputation," Brain, 121(Pt 4): 717-724, 1998.

Kumar, et al., "Deep Brain Stimulation for Intractable Pain: a 15-Year Experience," Neurosurgery, 40(4): 736-747, 1997.

Lange, et al., "Enlarged Amygdala Volume and Reduced Hippocampal Volume in Young Women with Major Depression," Psychological Medicine vol. 34, 2004, pp. 1059-1064.

Langguth, Berthold, et al.; NeuroReport—Neuronavigated rTMS in a patient with chronic tinnitus. Effects of 4 weeks treatment; Auditory and Vestibular Systems, 14(7):977-980, 2003.

Laszig, Roland, et al.; Benefits of Bilateral Electrical Stimulation with the Nucleus Cochlear Implant in Adults: 6-Month Postoperative Results; Otology & Neurotology, 25:958-968, 2004.

Lee, et al., "Discharge profiles of ventral tegmental area GABA neurons during movement, anesthesia, and the sleep-wake cycle," J. Neurosci., 21(5): 1757-66, 2001.

Leinonen, L., et al.; Functional Properties of Neurons in the Temporo-parietal Association Cortex of Awake Monkey; Exp. Brain Res., 39:203-215, 1980.

Lende, et al., "Relief of facial pain after combined removal of precentral and postcentral cortex," J. Neurogurg., 34: 537-543, 1971.

Lenz, et al., "Characteristics of the bursting pattern of action potentials that occurs in the thalamus of patients with central pain," Brain Res., 496(1-2): 357-360, 1989.

Lenz, F. A., et al.; Neuronal Activity in the region of the Thalamic Principal Sensory Nucleus (Ventralis Caudalis) in Patients with Pain Following Amputations; Neuroscience, 86(4):1065-1081, 1998.

Lever, et al., "Brain-derived neurotrophic factor is released in the dorsal horn by distinctive patterns of afferent fiber stimulation," J. Neurosci., 21(12): 4469-77, 2001.

Levy, et al., "Treatment of chronic pain by deep brain stimulation: long term follow-up and review of the literature," Neurosurgery, 21(6): 885-893, 1987.

Lisman, John E.; Bursts as a unit of neural information: making unreliable synapses reliable; Trends Neurosci., 20(1):38-43, 1997.

Lotze, et al., "Phantom movements and pain. An fMRI study in upper limb amputees," Brain, 124(Pt 11): 2268-2277, 2001.

Massaux, et al., "Auditory thalamus bursts in anesthetized and non-anesthetized states: contribution to functional properties," J. Neurophysiol., 91(5): 2117-34, 2004.

Matveev, "Differential short-term synaptic plasticity and transmission of complex spike trains: to depress or to facilitate," Cerebral Cortex, 10(11): 1143-1153, 2000.

McCormick, et al., "Corticothalamic activation modulates thalamic firing through glutamate "metabotropic" receptors," Proc. Natl. Acad. Sci. USA, 89(7): 2774-8, 1992.

McIntyre, Cameron C., et al.; Extracellular Stimulation of Central Neurons: Influence of Stimulus Waveform and Frequency on Neuronal Output; J. Neurophysiol., 88:1592-1604, 2002.

Merzenich, et al., "Somatosensory cortical map changes following digit amputation in adult monkeys," J. Comp. Neurol., 224(4): 591-605, 1984.

Miller, et al., "Feature selectivity and interneuronal cooperation in the thalamocortical system," J. Neurosci., 21(20): 8136-44, 2001.

Mirz, et al., "Positron emission tomography of cortical centers of tinnitus," Hearing Research, 134:133-144, 1999.

Moller, "Similarities between chronic pain and tinnitus," Am. J. Otol., 18: 577-585, 1997.

Moller, et al., "Some forms of tinnitus may involve the extralemniscal auditory pathway," Laryngoscope, 102:1165-1171, 1992.

Moller, et al., "The non-classical auditory pathways are involved in hearing in children but not in adults," Neuroscience Letters, 319: 41-44, 2002.

Mooney, et al., "Distinct forms of cholinergic modulation in parallel thalamic sensory pathways," Proc. Natl. Acad. Sci. USA, 101(1): 320-4, 2004.

Nguyen, et al., "Treatment of deafferentation pain by chronic stimulation of the motor cortex: report of a series of 20 cases," Acta Neurochir. Suppl., 68: 54-60, 1997.

Nikolajsen, et al., "Phantom limb pain," Br. J. Anaesth., 87(1): 107-16, 2001.

Norton, "Can ultrasound be used to stimulate nerve tissue?" Biomedical Engineering Online, 2: 6, 2003.

Oleskevich, et al., "Synaptic transmission in the auditory brainstem of normal and congenitally deaf mice," J. Physiol., 540(Pt 2): 447-55, 2002.

Perez-Reyes, "Molecular physiology of low-voltage-activated t-type calcium channels," Physiol. Rev., 83(1): 117-61, 2003.

Peyron, et al., "Functional imaging of brain responses to pain. A review and meta-analysis (2000)," Neurophysiol. Clin., 30(5): 263-88, 2000.

Phillips, et al., "Neurobiology of Emotion Perception I: The Neural Basis of Normal Emotion Perception," Biol Psychiatry vol. 54, 2003, pp. 504-514.

Phillips, et al., "Neurobiology of Emotion Preception II: Implications for Major Psychiatric Disorders," Biol Psychiatry vol. 54, 2003, pp. 515-528.

Pons, et al., "Massive cortical reorganization after sensory deafferentation in adult macaques," Science, 252(5014): 1857-1860, 1991.

Ramachandran, "Behavioral and magnetoencephalographic correlates of plasticity in the adult human brain," Proc. Natl. Acad. Sci. USA, 90(22): 10413-20, 1993.

Ramachandran, et al., "Cellular mechanisms underlying activity patterns in the monkey thalamus during visual behavior," J. Neurophysiol., 84(4): 1982-7, 2000.

Ramachandran, et al., "The perception of phantom limbs. The D. O. Hebb lecture," Brain, 121(Pt 9): 1603-1630, 1998.

Rauch, "Neuroimaging and neurocircuitry models pertaining to the neurosurgical treatment of psychiatric disorders," Neurosurg. Clin. N. Am., 14(2): 213-23, vii-viii, 2003.

Rinaldi, et al., "Spontaneous neuronal hyperactivity in the medial and intralaminar thalamic nuclei of patients with deafferentation pain," J. Neurosurg., 74: 415-421, 1991.

Sander, et al., "The Human Amygdala: An Evolved System for Relevance Detection," Reviews in Neurosciences vol. 14, 2003, pp. 303-316.

Sanes, et al., "Metabotropic glutamate receptor activation modulates sound level processing in the cochlear nucleus," J. Neurophysiol., 80(1): 209-17, 1998.

Schwindt, et al., "Mechanisms underlying burst and regular spiking evoked by dendritic depolarization in layer 5 cortical pyramidal neurons," Neurophysiol., 81(3): 1341-54, 1999.

Sherman, "A wake-up call from the thalamus," Nat. Neurosci., 4(4): 344-6, 2001.

Sherman, et al., "Chronic phantom and stump pain among American veterans: results of a survey," Pain, 18(1): 83-95, 1984.

Suga, et al., "Sharpening of frequency tuning by inhibition in the thalamic auditory nucleus of the mustached bat," J. Neurophysiol., 77(4): 2098-114, 1997.

Tardif, et al., "Patterns of calcium-binding proteins in human inferior colliculus: identification of subdivisions and evidence for putative parallel systems," Neuroscience, 116: 1111-1121, 2003.

Theuvenet, et al., "Responses to median and tibial nerve stimulation in patients with chronic neuropathic pain," Brain Topogr., 11(4): 305-313, 1999.

Tonndorf, "The analogy between tinnitus and pain: a suggestion for a physiological basis of chronic tinnitus," Hear. Res., 28(2-3): 271-275, 1987.

Tsubokawa, et al., "Chronic motor cortex stimulation for the treatment of central pain," Acta Neurochir. Suppl., 52: 137-139, 1991.

Tsubokawa, et al., "Treatment of thalamic pain by chronic motor cortex stimulation," Pacing Clin. Electrophysiol., 14(1): 131-134, 1991.

Urbain, et al., "The switch of subthalamic neurons from an irregular to a bursting pattern does not solely depend on their GABAergic inputs in the anesthetic-free rat," J. Neurosci., 22(19): 8665-8675, 2002.

Velasco, et al., "Centromedian-thalamic and hippocampal electrical stimulation for the control of intractable epileptic seizures," J. Clin. Neurophysiology, 18(6): 495-513, 2001.

Videbech, et al., "Hippocampal Volume and Depression: A Meta-Analysis of MRI Studies," Am. J. Psychiatry vol. 161, No. 11, Nov. 2004, pp. 1957-1966.

Vonck, et al., "Long-term amygdalohippocampal stimulation for refractory temporal lobe epilepsy," Ann. Neurol., 52: 556-565, 2002.

Vonck, et al., "Long-term deep brain stimulation for refractory temporal lobe epilepsy," Epilepsia, 46(Suppl. 5): 98-99, 2005.

Wallhausser-Franke, et al., "Expression of c-fos in auditory and non-auditory brain regions of the gerbil after manipulations that induce tinnitus," Experimental Brain Research, 153: 649-654, 2003.

Wan, et al., "Synaptic transmission of chaotic spike trains between primary afferent fiber and spinal dorsal horn neuron in the rat," Neuroscience, 125(4): 1051-60, 2004.

Weiss, et al., "Rapid functional plasticity of the somatosensory cortex after finger amputation," Exp. Brain Res., 134(2): 199-203, 2000.

Weissman, et al., "Cross-National Epidemiology of Major Depression and Bipolar Disorder," JAMA vol. 276, No. 4, Jul. 24-31, 1996, pp. 293-299.

Weisz, et al., "Abnormal auditory mismatch response in tinnitus sufferers with high-frequency hearing loss is associated with subjective distress level," BMC Neurosci., 5(1): 8, 2004.

Wu, et al., "Contribution of AMPA, NMDA, and GABA(A) receptors to temporal pattern of postsynaptic responses in the inferior colliculus of the rat," J. Neurosci., 24(19): 4625-34, 2004.

Yuste, et al., "Development and plasticity of the cerebral cortex: from molecules to maps," J. Neurobiol., 41(1): 1-6, 1999.

Zhang, et al., "Fos-like immunoreactivity in auditory and nonauditory brain structures of hamsters previously exposed to intense sound," Experimental Brain Research, 153: 655-660, 2003.

Results from Amytal Test

| INITIALS | AGE/ SEX | TINNITUS SIDE | TINNITUS FREQUENCY | TINNITUS INTENSITY | TINNITUS DURATION | TMS | IPSILATERAL AMYTAL TEST SUPRESSION | CONTRALATERAL AMYTAL TEST SUPRESSION |
|---|---|---|---|---|---|---|---|---|
| DG | 68 M | L | 8000 Hz | 10 dB | 10 Y | 0% | 25% | 60% PEEP GONE WHITE NOISE REMAINS |
| WC | 59 M | R | 8000 Hz | 10 dB | 5 Y | 0% | 30% | 60% HEAVENLY FEELING DISINTEREST IN TINNITUS |
| DM | 69 M | R | ? | ? | 9 Y | 50% | 0% | 70% EMOTIONALLY UNCHANGED |
| DCA | 47 M | BIL | 6500 Hz | 5 dB | 5 Y | 25% | 0% | 0% |
| BA | 43 M | BIL | 8000 Hz | 25 dB | 1 Y | 0% | 10% | 10% |

FIG. 5

STIMULATION OF THE AMYGDALOHIPPOCAMPAL COMPLEX TO TREAT NEUROLOGICAL CONDITIONS

RELATED APPLICATIONS

This application is a continuation of U.S. application Ser. No. 12/577,640, filed Oct. 12, 2009, now U.S. Pat. No. 8,239,029, which is a continuation of U.S. application Ser. No. 11/254,612, filed Oct. 20, 2005, now U.S. Pat. No. 7,603,174, which claims the benefit of U.S. Provisional Application Nos. 60/620,847 filed Oct. 21, 2004, 60/631,089 filed Nov. 24, 2004 and 60/639,365 filed Dec. 27, 2004, the disclosures of which are fully incorporated herein by reference.

This application is also related to U.S. Provisional Application Nos. 60/620,762 filed Oct. 21, 2004, 60/631,085 filed Nov. 24, 2004, 60/620,827 filed Oct. 21, 2004, 60/631,091 filed Nov. 24, 2004, and 60/620,781 filed Oct. 21, 2004 each of which is incorporated by reference in its entirety.

TECHNICAL FIELD

This invention relates to deep brain stimulation to treat neurological condition or disorders, more particularly, deafferentation disorder (e.g., tinnitus and phantom pain), and affective disorders.

BACKGROUND OF THE INVENTION

A. Auditory Dysfunction

Auditory dysfunctions are common. For example, in the United States, the prevalence of tinnitus when the whole population is considered is approximately 3%. This prevalence is only 1% under the age of 45 but increases significantly with age, rising to 9% in the population over 65 years (Adams et al., 1999). This roughly translates to 36 million Americans with tinnitus (Heller 2003) Tinnitus is a noise in the ears, often described as ringing, buzzing, roaring, or clicking Subjective and objective forms of tinnitus exist, with objective tinnitus often caused by muscle contractions or other internal noise sources in the area proximal to auditory structures. In certain cases, external observers can hear the sound generated by the internal source of objective tinnitus. In subjective forms, tinnitus is audible only to the subject. Tinnitus varies in perceived amplitude, with some subjects reporting barely audible forms and others essentially deaf to external sounds and/or incapacitated by the intensity of the perceived noise.

Because auditory dysfunction often occurs secondary to a pathological state, initial treatment may focus on finding an underlying cause. A subject presenting with, for example, tinnitus may be asked for information regarding medications, recent or chronic noise exposure, and home and work environment. Common medications such as aspirin are known to cause tinnitus in some patients or in elevated dosages. Stress can be a direct cause of tinnitus and can aggravate existing cases. A thorough physical exam is typically made of a subject with complaints of tinnitus to eliminate pathologies such as hypertension, tumors, and infections. Objective tinnitus may be diagnosed using a stethoscope if the source of the noise can be localized. For example, hypertension or arterial disorders may produce objective tinnitus, as the carotid arteries pass close to the auditory organs in humans, and excessive pressure or arterial blockage may cause detectible noise to both the subject and to an outside observer.

If a treatable underlying cause to the auditory dysfunction is identified, treatment may focus on elimination of the cause. For example, hypertensive patients may see a reduction or elimination of tinnitus once anti-hypertensive therapy begins. However, a significant number of patients have untreatable underlying pathologies or have auditory dysfunction in the absence of any identifiable cause. For these patients, treatments for directly reducing or eliminating the auditory dysfunction are desirable.

Tinnitus research is actively pursued in the hope of finding efficacious treatments. Recently published work has utilized drug delivery systems such as the system described in U.S. Pat. No. 5,713,847, which includes a catheter inserted into a patient's auditory cortex or thalamus for microinfusing drugs.

Another example of published drug delivery techniques is U.S. Pat. No. 6,656,172, which describes a tinnitus treatment that includes inserting intrathecally a catheter for infusing a drug. Other treatment methods may try to mask the perceived tinnitus noise by generating an audible signal of appropriate frequency. WO 01/08617 describes a system with a vibrating probe placed in proximity to the inner ear.

Nerve stimulation has been shown to be helpful in treating patients with chronic intractable pain. For those patients who prove unresponsive to conservative pain management techniques, peripheral nerve stimulation may be a successful therapy for pain management when the pain is known to result from a specific nerve. Peripheral nerve stimulation is based in part on the Melzack-Wall gate control theory of pain. Sweet and Wespic first used electrical stimulation of peripheral nerves in the 1960s to mask the sensation of pain with a tingling sensation (paresthesia) caused by the electrical stimulation. Subsequent refinements in the technology, surgical technique and patient selection have led to improved long term results.

B. Depression

Depression is an important public health problem affecting about 15% of the general population (Rauch 2003). The lifetime rates for major depression vary widely across countries, ranging from 1.5 cases per 100 adults in the sample in Taiwan to 19.0 cases per 100 adults in Beirut. The annual rates range from 0.8 cases per 100 adults in Taiwan to 5.8 cases per 100 adults in New Zealand. The mean age at onset shows less variation (range, 24.8-34.8 years). In every country, the rates of major depression are higher for women than men. Insomnia and loss of energy occur in most persons with major depression at each site. Persons with major depression are also at increased risk for co-morbidity with substance abuse and anxiety disorders at all sites. Persons who were separated or divorced have significantly higher rates of major depression than married persons in most of the countries, and the risk is somewhat greater for divorced or separated men than women in most countries (Weissman, Bland et al. 1996).

Efforts have been made to treat psychiatric disorders with peripheral/cranial nerve stimulation. Recently, partial benefits with vagus nerve stimulation in patients with depression have been described in U.S. Pat. No. 5,299,569. Another example of electrical stimulation to treat depression is described in U.S. Pat. No. 5,470,846, which discloses the use of transcranial pulsed magnetic fields to treat depression. Yet further, U.S. Pat. No. 5,263,480 describes that stimulation of the vagus nerve may control depression and compulsive eating disorders and U.S. Pat. No. 5,540,734 teaches stimulation of the trigeminal or glossopharyngeal nerves for psychiatric illness, such as depression.

Significant advances in the treatment of depression have been made in the past decade. Since the introduction of selective serotonin reuptake inhibitors (SSRIs), i.e., Prozac®, many patients have been effectively treated with anti-depressant medication. New medications to treat depression are introduced almost every year, and research in this area is ongoing. However, an estimated 10 to 30 percent of depressed patients taking an anti-depressant are partially or totally resistant to the treatment. Those who suffer from treatment-resistant depression have almost no alternatives. Thus, there is a need to develop alternative treatments for these patients.

C. Deep Brain Stimulation to Treat Neurological Conditions

Deep brain stimulation (DBS) has been applied to the treatment of central pain syndromes and movement disorders, and it is currently being explored as a therapy for epilepsy. For instance, U.S. Pat. No. 6,016,449 and U.S. Pat. No. 6,176,242 disclose a system for the electrical stimulation of areas in the brain for the treatment of certain neurological diseases such as epilepsy (See Vonck et al., 2005; Vonck et al., 2002 and Velasco et al., 2001), cluster headaches (Benabid, Wallace et al. 2005) and Parkinson's disease (Benabid, Wallace et al. 2005).

The use of stimulating electrodes to treat tinnitus has been published. U.S. Pat. Nos. 5,735,885 and 5,496,369 describe the placement of an electrode in the primary auditory cortex of a patient. U.S. Pat. Nos. 6,456,886 and 5,697,975 also use an electrode placed in the auditory cortex, and further describe placement of an electrode in the medial geniculate body of the thalamus.

Thus, various electrical stimulation and/or drug infusion devices have been proposed for treating neurological disorders. Some devices stimulate through the skin, such as electrodes placed on the scalp. Other devices require significant surgical procedures for placement of electrodes, catheters, leads, and/or processing units. These devices may also require an external apparatus that needs to be strapped or otherwise affixed to the skin.

However, despite the aforesaid available treatments, there are patients with major depression, auditory dysfunction and other neurological conditions that remain disabled. For these severely ill and disabled patients, novel therapies are required. Thus, the present invention is the first to utilize deep brain stimulation to treat a variety of neurological conditions, for example depression and auditory dysfunction.

BRIEF SUMMARY OF THE INVENTION

Embodiments of the present invention comprise a therapeutic system for treating a neurological condition or disorder having a surgically implanted device in communication with a predetermined brain region, for example the amygdala, hippocampus, parahippocampus, perirhinal cortex, and entorhinal cortex. The device can include a distal probe, such as, for example, an electrode assembly or electrical stimulation lead. The proximal end of the probe is coupled to an electrical signal source, which, in turn, is operated to stimulate the predetermined brain region.

In certain embodiments of the present invention, the neurological disorder and/or condition is an auditory dysfunction, for example, but not limited to tinnitus, hyperacousis, phonophobia, misophonia, auditory agnosia, auditory spatial dysfunction or auditory hallucinations. Yet further, the neurological disorder and/or condition can be a mood and/or anxiety disorder, for example, but not limited to depression, biopolar dysthymic disorder, panic disorder, posttraumatic stress disorder, obsessive-compulsive disorder, phobic disorder. In further embodiments, the neurological disorder and/or condition is phantom pain.

Other stimulation devices used in certain embodiments are drug pumps which provide chemical stimulation of a predetermined brain region. Chemical stimulation can be provided by delivery of pharmaceuticals or neuroactive substances that, for example, disrupt or block pathological activity.

Magnetic stimulation of certain brain regions for the treatment of neurological conditions and/or disorders is used in certain embodiments of the present invention. Magnetic stimulation can be provided by internally implanted probes or by externally applied directed magnetic fields.

Yet further, thermal stimulation can be provided via implanted probes that are regulated to heat and/or cold temperatures. In other embodiments, ultrasound stimulation is used as a stimulation source, either by itself or in combination with another stimulation source. For example, in certain embodiments of the invention, ultrasound is used to stimulate active tissue by propagating ultrasound in the presence of a magnetic field as described by Norton (2003), herein incorporated by reference in its entirety. Combinations of stimulation sources are used in some embodiments of the invention.

Devices used with the invention can operate with various stimulation parameters. One example of stimulation parameters used with an electrical stimulation device to treat neurological conditions and/or disorders uses an amplitude in the range of about 2 mA to about 100 mA, a frequency in the range of about 3 Hz to about 50 Hz, and a pulse width in the range of about 5 microseconds to about 100 microseconds. However, other parameters are used in other embodiments of the invention, such as, for example, higher and lower frequencies, various current amplitudes, and/or pulse width durations. In another embodiment of the invention, a frequency stimulation parameter of about 80 Hz is used. Burst mode stimulation is used in preferred embodiments of the invention. The burst stimulus comprises a frequency in the range of about 1 Hz to about 300 Hz, more particular, in the range of about 1 Hz to about 12 Hz, and more particularly, in the range of about 1 Hz to about 4 Hz, 4 Hz to about 7 Hz or about 8 Hz to about 12 Hz, 18 Hz to 20 Hz, and 40 Hz. The burst stimulus comprises at least two spikes, for example, each burst stimulus can comprise about 2 to about 100 spikes, more particularly, about 2 to about 10 spikes. Each spike can comprise a frequency in the range of about 50 Hz to about 1000 Hz, more particularly, in the range of about 200 Hz to about 500 Hz. The interval between spikes can be about 0.5 milliseconds to about 100 milliseconds. More particularly, the maximum inter-spike interval may be about 5 milliseconds. Those of skill in the art realize that this can vary depending upon the patient and the treatment. The frequency of the spikes within the burst does not need to be constant or regular, in fact, typically, the frequency of the spikes is random or variable. In further embodiments, the burst stimulus is followed by an inter-burst interval. The inter-burst interval has a duration in the range of about 5 milliseconds to about 5 seconds, more preferably, in the range of about 10 milliseconds to about 300 milliseconds, or any range therebetween, for example, the minimum inter-burst interval may be about 20 milliseconds. It is envisioned that the burst stimulus has a duration in the range of about 10 milliseconds to about 5 seconds, more particularly in the range of about 250 milliseconds to 1 second. The burst stimulus and the inter-burst interval can have a regular pattern or an irregular pattern (e.g., random or irregular harmonics).

The invention also comprises a method for treating neurological conditions and/or disorders. The method comprises surgically implanting an electrical stimulation lead such as a multiple electrode lead. Following implantation, the proximal end of the lead is attached to a signal generator. The signal generator then generates a signal that stimulates a predetermined brain region.

In some embodiments of the invention, electrical stimulation parameters are varied after implantation to optimize treatment of a neurological disorder or condition. The parameters varied may include modification of the predetermined implantation site, or modification of, for example, signal amplitude, frequency, pulse width or pulse shape of the stimulation signal.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 5 is a table showing the results of an amytal test.

DETAILED DESCRIPTION OF THE INVENTION

I. Definitions

Figure 1A:
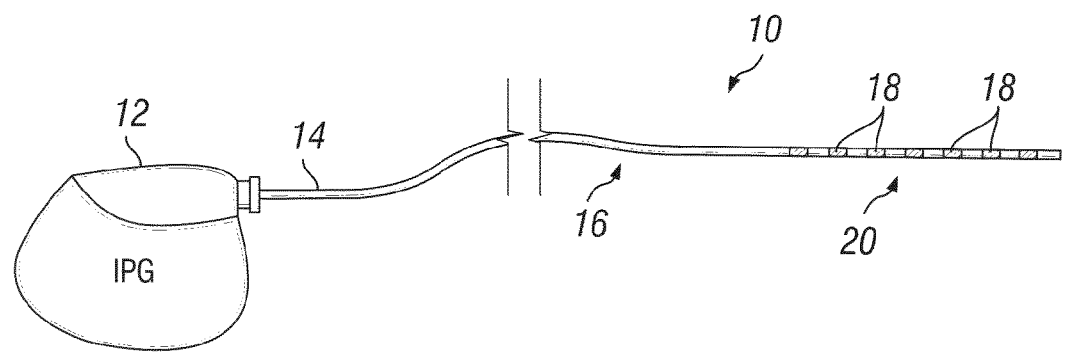
FIGS. 1A and 1B illustrate example electrical stimulation systems.

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

As used herein the term "affective disorders" refers to a group of disorders that are commonly associated with co-morbidity of depression and anxiety symptoms.

As used herein the term "anxiety" refers to an uncomfortable and unjustified sense of apprehension that may be diffuse and unfocused and is often accompanied by physiological symptoms.

As used herein the term "anxiety disorder" refers to or connotes significant distress and dysfunction due to feelings of apprehension, guilt, fear, etc. Anxiety disorders include, but are not limited to panic disorders, posttraumatic stress disorder, obsessive-compulsive disorder and phobic disorders.

As used herein, the term "depression" refers to a morbid sadness, dejection, or melancholy.

As used herein, the terms "amygdala" and "amygdalohippocampal complex" or "amygdaloid complex" or "amygdaloid nucleus" refer to the gray and white matter associated with the amygdala, as well as the projections associated with, or projecting to and/or from the amygdala, for example, projections associated with the hippocampus. The amygdala is an almond-shaped brain region located in the medial temporal lobes of the brain. It is a subcortical structure located at the dorsomedial tip of the temporal lobe and continuous with the uncus of the parahippocampal gyms. The amygdala comprises several separately-functioning nuclei that have been grouped together by their anatomical proximity, including the basl and lateral nuclei, the central nucleus, the cortical nuclei, and medial nuclei. Those of skill in the art are aware that the nuclei that compose the amygdala are reciprocally connected to the hypothalamus, hippocampal formation, neocortex, and thalamus. As used herein, the term amygdala includes the defined area of the amygdala as known by one of skill in the art, as well as the surrounding or adjacent gray matter or white matter tracts leading to and from amygdala and/or gray matter or white matter tracts that are contiguous with amygdala. The surrounding or adjacent gray matter or white matter can include up to approximately a 1 cm radius of amygdala.

As used herein, the term "auditory dysfunction" refers to conditions or dysfunctions associated with the auditory pathway. Such auditory dysfunctions can include, but are not limited to tinnitus, hyperacousis, phonophobia, misophonia, auditory agnosia in all its forms, auditory spatial dysfunction (localizing sound) and auditory hallucinations, inclusive of musical hallucinosis. Auditory hallucinations can occur in schizophrenia or use of certain drugs (e.g., antimuscarinic agents, antiparkinsonian drugs, antidepressants, beta adrenoceptor antagonists and opiates). Auditory dysfunction can also include hearing loss. Hearing loss can be conductive hearing loss (mechanical transmission of sound into the sensory receptors in the cochlea is impaired), sensorineural hearing loss (a loss of function in the sensory receptors in either the cochlea or the auditory nerve), or central hearing loss (a lesion in the brain stem or auditory cortex).

As used herein, the terms "auditory nerve" and "cochlear nerve" are interchangeable and refer to the nerve fibers along which the sensory cells of the ear communicate information to the brain. The auditory or cochlear nerve are part of the vestibulocochlear nerve which carries two kinds of sensation, vestibular (balance) and audition (hearing) from sensory receptors in the inner ear. The auditory nerve consists of the vestibular nerve and the cochlear nerve. The vestibulocochlear nerve is also known as the eighth cranial nerve.

As used herein, the term "brain region" refers to any tissue comprising that part of the central nervous system contained within the cranium. The brain stem tissue is also encompassed by the term brain region, including the diencephalon.

As used herein, the term "in communication" refers to the stimulation lead being adjacent, in the general vicinity, in close proximity, or directly next to or directly on the predetermined stimulation site. Thus, one of skill in the art understands that the lead is "in communication" with the predetermined site if the stimulation results in a modulation of neuronal activity. In certain embodiments, the predetermined site is the amygdalohippocampal complex or amygdaloid complex.

As used herein the term "limbic system" encompasses the amygdala, hippocampus, septum, cingulate gyms, cingulate cortex, hypothalamus, epithalamus, anterior thalamus, mammillary bodies, nucleus accumbens, fornix, parahippocampus, perirhinal cortex, and entorhinal cortex. The limbic system has connections throughout the brain, more particularly with the primary sensory cortices, including the rhinencephalon for smell, the autonomic nervous system via the hypothalamus, and memory areas. Yet further, the limbic system is involved in mood, emotion and thought. Two limbic or paralimbic divisions have been described, one associated with the archencephalic hippocampus, one associated with the paleocephalic amygdala. The hippocampal division connects predominantly to the following structures: hippocampus, posterior parahippocampal, retrosplenium, posterior cingulated cortex, and the supracallosal cingulated cortex. The hippocampal division is involved in explicit processing, memory encoding, visual spatial analysis, skeletomotor effector, attentional and motivational functions. The amygdala division connects predominantly to the anterior parahipocampal area, the insula, temporal pole, infracallosal cingulated cortex and the orbitofrontal cortex. The amygdala division is involved in implicit processing, visceral integration, visual feature analysis, appetite drives, social awareness and mood (Cummings and Mega 2003).

As used herein the term "modulate" refers to the ability to regulate positively or negatively neuronal activity. Thus, the term modulate can be used to refer to an increase, decrease, masking, altering, overriding or restoring of neuronal activity.

As used herein, the term "burst firing" or "burst mode" or "burst mode stimulation" refers to an action potential that is a burst of high frequency spikes (300-1000 Hz) (Beurrier et al., 1999). Burst firing acts in a non-linear fashion with a summation effect of each spike. One skilled in the art is also aware that burst firing can also be referred to as phasic firing, rhythmic firing (Lee 2001), pulse train firing, oscillatory firing and spike train firing, all of these terms used herein are interchangeable.

As used herein, the term "tonic firing" or "tonic mode" refers to an action potential that occurs in a linear fashion.

As used herein, the term "burst" refers to a period in a spike train that has a much higher discharge rate than surrounding periods in the spike train (N. Urbain et al., 2002). Thus, burst can refer to a plurality of groups of spike pulses. A burst is a train of action potentials that occurs during a 'plateau' or 'active phase', followed by a period of relative quiescence called the 'silent phase' (Nunemaker, Cellscience Reviews Vol 2 No. 1, 2005.) Thus, a burst comprises spikes having an inter-spike interval in which the spikes are separated by 0.5 milliseconds to about 100 milliseconds. Those of skill in the art realize that the inter-spike interval can be longer or shorter. Yet further, those of skill in the art also realize that the spike rate within the burst does not necessarily occur at a fixed rate; this rate can be variable.

As used herein, the term "spike" refers to an action potential. Yet further, a "burst spike" refers to a spike that is preceded or followed by another spike within a short time interval (Matveev, 2000), in otherwords, there is an inter-spike interval, in which this interval is generally about 10 ms but can be shorter or longer, for example 5 milliseconds or 0.5 milliseconds.

As used herein, the term "neuronal" refers to a neuron which is a morphologic and functional unit of the brain, spinal column, and peripheral nerves.

As used herein, the term "neurology" or "neurological" refers to conditions, disorders, and/or diseases that are associated with the nervous system. The nervous system comprises two components, the central nervous system, which is composed of the brain and the spinal cord, and the peripheral nervous system, which is composed of ganglia and the peripheral nerves that lie outside the brain and the spinal cord. One of skill in the art realizes that the nervous system may be separated anatomically, but functionally they are interconnected and interactive. Yet further, the peripheral nervous system is divided into the autonomic system (parasympathetic and sympathetic), the somatic system and the enteric system. Thus, any condition, disorder and/or disease that effects any component or aspect of the nervous system (either central or peripheral) is referred to as a neurological condition, disorder and/or disease. As used herein, the term "neurological" or "neurology" encompasses the terms "neuropsychiatric" or "neuropsychiatry" and "neuropsychological" or "neuropsychological". Thus, a neurological disease, condition, or disorder includes, but is not limited to cognitive disorders, auditory disorders, affective disorders, movement disorders, mental disorders, pain disorders, sleep disorders, etc.

As used herein, the term "neuropsychiatry" or "neuropsychiatric" refers to conditions, disorders and/or diseases that relate to both organic and psychic disorders of the nervous system.

As used herein, the term "neuropsychological" or "neuropsychologic" refers to conditions, disorders and/or disease that relate to the functioning of the brain and the cognitive processors or behavior.

As used herein, the term "somatosensory system" refers to the peripheral nervous system division comprising primarily afferent somatic sensory neurons and afferent visceral sensory neurons that receive sensory information from skin and deep tissue, including the 12 cranial and 21 spinal nerves.

As used herein, the term "stimulate" or "stimulation" refers to electrical, chemical, thermal stimulation and/or magnetic stimulation and/or ultrasound stimulation that modulates neuronal tissue of brain regions. Ultrasound stimulation is used as a stimulation source, either by itself or in combination with another stimulation source. For example, in certain embodiments of the invention, ultrasound is used to stimulate active tissue by propagating ultrasound in the presence of a magnetic field as described by Norton (2003), herein incorporated by reference in its entirety.

As used herein, the term "treating" and "treatment" refers to modulating certain areas of the brain so that the subject has an improvement in the disease, for example, beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

II. Electrical Stimulation Sources

Figure 1B:
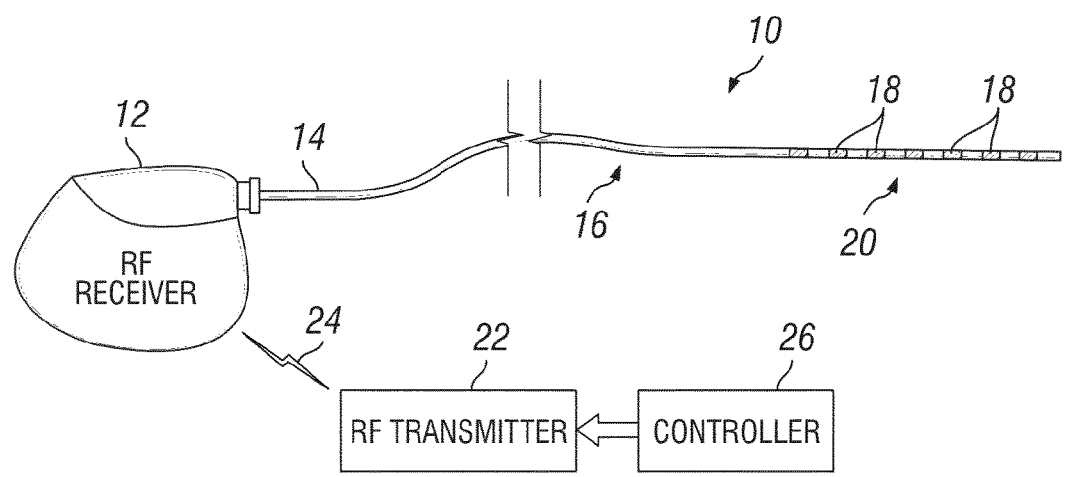
Figure 2A:
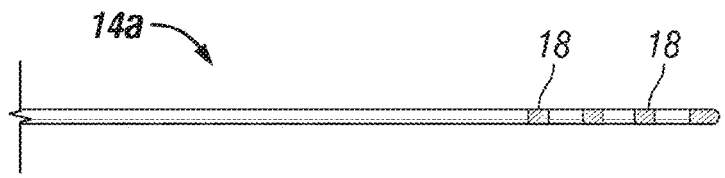
FIGS. 2A-2I illustrate example electrical stimulation leads that may be used to electrically stimulate brain regions.
Figure 2B:
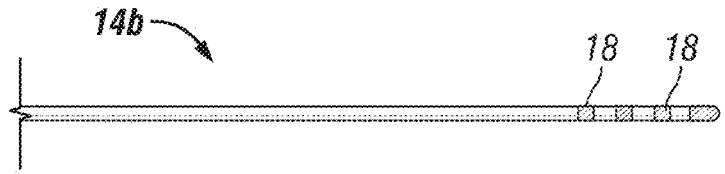
Figure 2C:
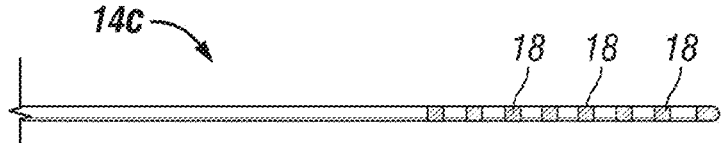
Figure 2D:
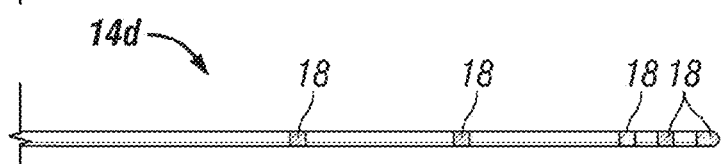
Figure 2E:
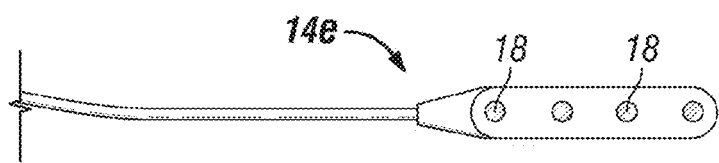
Figure 2F:
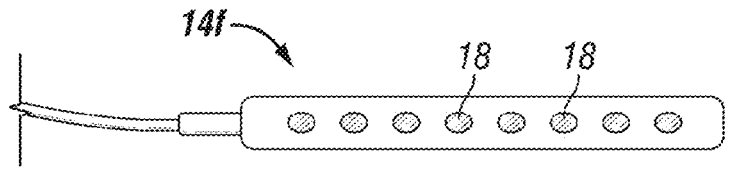
Figure 2G:
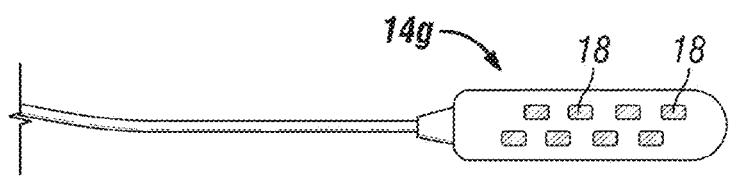
Figure 2H:
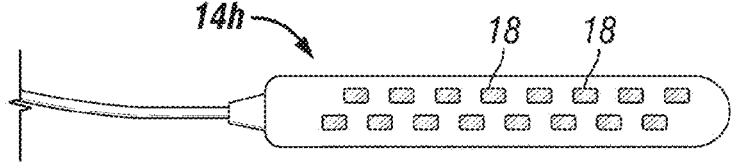
Figure 2I:
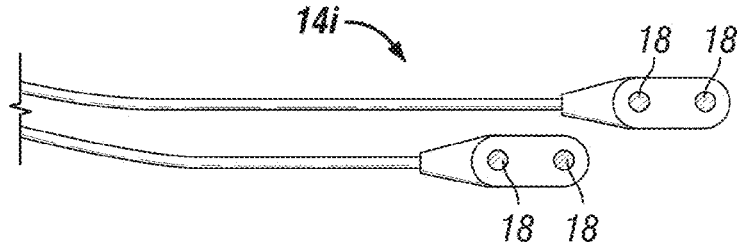

FIGS. 1A-1B illustrate example neurological stimulation systems 10 for electrically stimulating a predetermined brain region to treat auditory dysfunctions such as, for example, tinnitus, as well as treat other possible neurological conditions and/or diseases. In general terms, stimulation system 10 includes an implantable electrical stimulation source 12 and one or more implantable electrical stimulation leads 14 for applying electrical stimulation pulses to a predetermined site. In operation, one or both of these primary components are implanted in or on a subject's body, as discussed below. In certain embodiments, stimulation source 12 is coupled directly to a connecting portion 16 of stimulation lead 14. In certain other embodiments, stimulation source 12 is incorporated into the stimulation lead 14 and stimulation source 12 instead is embedded within stimulation lead 14. For example, such a stimulation system 10 may be a Bion® stimulation system manufactured by Advanced Bionics Corporation. Whether stimulation source 12 is coupled directly to or embedded within the stimulation lead 14, stimulation source 12 controls the stimulation pulses transmitted to one or more stimulation electrodes 18 located on a stimulating portion 20 of stimulation lead 14, positioned in communication with a predetermined site, according to suitable stimulation parameters (e.g., duration, amplitude or intensity, frequency, pulse width, etc.). One example of stimulation parameters used may use an amplitude in the range of about 2 mA to about 100 mA, a frequency in the range of about 3 Hz to about 50 Hz, and a pulse width in the range of about 5 microseconds to about 100 microseconds. However, other parameters are used in other embodiments of the invention, such as, for example, higher and lower frequencies, various current amplitudes, and/or pulse width durations. In another embodiment of the invention, a frequency stimulation parameter of about 80 Hz is used. The predetermined site in communication with the stimulation lead 14 is a brain region such as the amygdala or amygdaloahippocampal complex in a preferred embodiment. A doctor, the patient, or another user of stimulation source 12 may directly or indirectly input stimulation parameters to specify or modify the nature of the stimulation provided.

Preferred embodiments employ a burst stimulus. Examples of burst stimulus are found in U.S. application entitled "New Stimulation Design for Neuromodulation", filed Oct. 20, 2005, which is incorporated by reference. The burst stimulus comprises a frequency in the range of about 1 Hz to about 300 Hz, more particular, in the range of about 1 Hz to about 12 Hz, and more particularly, in the range of about 1 Hz to about 4 Hz, 4 Hz to about 7 Hz or about 8 Hz to about 12 Hz, 18 Hz to 20 Hz, and 40 Hz. The burst stimulus comprises at least two spikes, for example, each burst stimulus can comprise about 12 to about 100 spikes, more particularly, about 2 to about 10 spikes. Each spike can comprise a frequency in the range of about 50 Hz to about 1000 Hz, more particularly, in the range of about 200 Hz to about 500 Hz. The interval between spikes can be about 0.5 milliseconds to about 100 milliseconds. The frequency of the spikes within the burst does not need to be constant or regular, in fact, typically, the frequency of the spikes is random or variable. In further embodiments, the burst stimulus is followed by an inter-burst interval. The inter-burst interval has a duration in the range of about 5 milliseconds to about 5 seconds, more preferably, about 10 milliseconds to about 300 milliseconds. It is envisioned that the burst stimulus has a duration in the range of about 10 milliseconds to about 5 seconds, more particularly in the range of about 250 milliseconds to 1 second. The burst stimulus and the inter-burst interval can have a regular pattern or an irregular pattern (e.g., random or irregular harmonics).

In one embodiment, as shown in FIG. 1A, stimulation source 12 includes an implantable pulse generator (IPG). One of skill in the art is aware that any commercially available implantable pulse generator can be used in the present invention, as well as a modified version of any commercially available pulse generator. Thus, one of skill in the art would be able to modify an IPG to achieve the desired results. An exemplary IPG is one that is manufactured by Advanced Neuromodulation Systems, Inc., such as the Genesis® System, part numbers 3604, 3608, 3609, and 3644. Another example of an IPG is shown in FIG. 1B, which shows stimulation source 12 including an implantable wireless receiver. An example of a wireless receiver may be one manufactured by Advanced Neuromodulation Systems, Inc., such as the Renew® System, part numbers 3408 and 3416. In another embodiment, the IPG can be optimized for high frequency operation as described in U.S. Provisional Application Ser. No. 60/685,036, filed May 26, 2005, entitled "SYSTEMS AND METHODS FOR USE IN PULSE GENERATION," which is incorporated herein by reference. The wireless receiver is capable of receiving wireless signals from a wireless transmitter 22 located external to the person's body. The wireless signals are represented in FIG. 1B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the signal parameters of electrical signals transmitted through electrical stimulation lead 14 to the stimulation site. Thus, the external controller 26 can be for example, a handheld programmer, to provide a means for programming the IPG. An example wireless transmitter 122 may be one manufactured by Advanced Neuromodulation Systems, Inc., such as the Renew® System, part numbers 3508 and 3516.

Conventional neuromodulation devices can be modified to apply burst stimulation to nerve tissue of a patient by modifying the software instructions stored in the devices. Specifically, conventional neuromodulation devices typically include a microprocessor and a pulse generation module. The pulse generation module generates the electrical pulses according to a defined pulse width and pulse amplitude and applies the electrical pulses to defined electrodes. The microprocessor controls the operations of the pulse generation module according to software instructions stored in the device.

These conventional neuromodulation devices can be adapted by programming the microprocessor to deliver a number of spikes (relatively short pulse width pulses) that are separated by an appropriate inter-spike interval. Thereafter, the programming of the microprocessor causes the pulse generation module to cease pulse generation operations for an inter-burst interval. The programming of the microprocessor also causes a repetition of the spike generation and cessation of operations for a predetermined number of times. After the predetermined number of repetitions have been completed, the microprocessor can cause burst stimulation to cease for an amount of time (and resume thereafter). Also, in some embodiments, the microprocessor could be programmed to cause the pulse generation module to deliver a hyperpolarizing pulse before the first spike of each group of multiple spikes.

The microprocessor can be programmed to allow the various characteristics of the burst stimulus to be set by a physician to allow the burst stimulus to be optimized for a particular pathology of a patient. For example, the spike amplitude, the inter-spike interval, the inter-burst interval, the number of bursts to be repeated in succession, the amplitude of the hyperpolarizing pulse, and other such characteristics could be controlled using respective parameters accessed by the microprocessor during burst stimulus operations. These parameters could be set to desired values by an external programming device via wireless communication with the implantable neuromodulation device.

In another embodiment, a neuromodulation device can be implemented to apply burst stimulation using a digital signal processor and one or several digital-to-analog converters. The burst stimulus waveform could be defined in memory and applied to the digital-to-analog converter(s) for application through electrodes of the medical lead. The digital signal processor could scale the various portions of the waveform in amplitude and within the time domain (e.g., for the various intervals) according to the various burst parameters.

FIGS. 2A-2I illustrate example stimulation leads 14 that may be used for electrically stimulating a predetermined brain region for treating neurological conditions and/or disorders. As described above, each of the one or more stimulation leads 14 incorporated in stimulation system 10 includes one or more stimulation electrodes 18 adapted to be positioned in communication with the predetermined brain region and used to deliver the stimulation pulses received from stimulation source 12. A percutaneous stimulation lead 14, such as example stimulation leads 14a-d, includes one or more circumferential electrodes 18 spaced apart from one another along the length of stimulating portion 20 of stimulation lead 14. Circumferential electrodes 18 emit electrical stimulation energy generally radially (i.e., generally perpendicular to the axis of stimulation lead 14) in all directions. Directional stimulation electrodes 18 emit electrical stimulation energy in a direction generally perpendicular to the surface of stimulation lead 14 on which they are located. Although various types of stimulation leads 14 are shown as examples, the present invention contemplates stimulation system 10 including any suitable type of stimulation lead 14 in any suitable number. In addition, stimulation leads 14 may be used alone or in combination. For example, unilateral stimulation of an ipsilateral or contralateral side of a brain region may be accomplished using a single electrical stimulation lead 14 implanted in communication with the region in one hemisphere of the subject's brain, while bilateral electrical stimulation of the brain region may be accomplished using two stimulation leads 14 implanted in communication with the region in both brain hemispheres. Multi-region implantation of stimulation leads can be used.

In one embodiment, the stimulation source is transcutaneously in communication with the electrical stimulation lead. In "transcutaneous", electrical nerve stimulation (TENS) the stimulation source is external to the patient's body, and may be worn in an appropriate fanny pack or belt, and the electrical stimulation lead is in communication with the stimulation source, either remotely or directly.

In addition to electrical stimulation, other forms of stimulation can be used, for example magnetic. Magnetic stimulation can be provided by internally implanted probes or by externally applied directed magnetic fields, for example, U.S. Pat. Nos. 6,592,509; 6,132,361; 5,752,911; and 6,425,852, each of which is incorporated herein in its entirety. Quick pulses of magnetic stimulation can be applied externally or transcranially, for example repetitive transcranially magnetic stimulation (rTMS).

Whether using percutaneous leads, laminotomy leads, or some combination of both, the leads are coupled to one or more conventional neurostimulation devices, or signal generators. The devices can be totally implanted systems and/or radio frequency (RF) systems. An example of an RF system is a MNT/MNR-916CC system manufactured by Advanced Neuromodulation Systems, Inc.

The preferred neurostimulation devices should allow each electrode of each lead to be defined as a positive, a negative, or a neutral polarity. For each electrode combination (e.g., the defined polarity of at least two electrodes having at least one cathode and at least one anode), an electrical signal can have at least a definable amplitude (e.g., voltage), pulse width, and frequency, where these variables may be independently adjusted to finely select the sensory transmitting nerve tissue required to inhibit transmission of neuronal signals. Generally, amplitudes, pulse widths, and frequencies are determinable by the capabilities of the neurostimulation systems, which are known by those of skill in the art. Voltages that may be used can include, for example about 0.5 to about 10 volts, more preferably about 1 to about 10 volts.

It is envisaged that the patient will require intermittent assessment with regard to patterns of stimulation. Different electrodes on the lead can be selected by suitable computer programming, such as that described in U.S. Pat. No. 5,938,690, which is incorporated by reference here in full. Utilizing such a program allows an optimal stimulation pattern to be obtained at minimal voltages. This ensures a longer battery life for the implanted systems.

III. Implantation of Stimulation Sources

Figure 3:
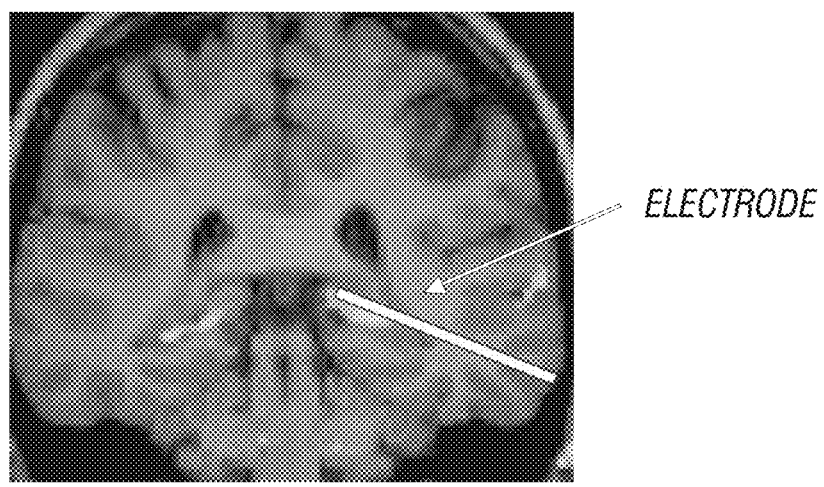
FIG. 3 illustrates example placement of a single stimulation lead and stimulation electrode in communication with the amygdalohippocampal complex.

FIG. 3 illustrates example placement of a single stimulation lead for electrical stimulation of the amygdalohippocampal complex by a stimulation electrode. Placement of the stimulation electrode is visualized by x-ray monitoring or other visualization means during implantation. The brain region to be stimulated is predetermined before implantation using such medical imaging tools as magnetic resonance imaging, computerized axial tomography, and positron emission tomography. Multiple stimulation leads and electrodes are used in other embodiments of the invention. It is understood by one of ordinary skill in the art that brain regions are not well defined and that individual variations make exact placement of the stimulation electrode vary according to the patient's anatomy and pathology. Certain embodiments of the invention contemplate a stimulation electrode in communication with the amygdalohippocampal complex and the illustration in FIG. 3 is an approximation of the predetermined placement for the patient imaged.

In other embodiments, the neurological condition or disorder to be treated may require stimulation of additional or alternative areas. For example, in certain embodiments of the invention, the neurological condition or disorder which can treated by stimulation of limbic system components, such as, for example, the amygdala, hippocampus, parahippocampus, perirhinal cortex, and entorhinal cortex.

While not being bound by the description of a particular procedure, patients who are to have an electrical stimulation lead or electrode implanted into the brain, generally, first have a stereotactic head frame, such as the Leksell, CRW, or Compass, mounted to the patient's skull by fixed screws. However, frameless techniques may also be used. Subsequent to the mounting of the frame, the patient typically undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The current way to do this is to rigidly mount the head frame to the surgical table. Subsequently, a series of reference points are established to relative aspects of the frame and the patient's skull, so that either a person or a computer software system can adjust and calculate the correlation between the real world of the patient's head and the virtual space model of the patient's MRI scans. The surgeon is able to target any region within the stereotactic space of the brain with precision (i.e., within 1 mm). Initial anatomical target localization is achieved either directly using the MRI images, or indirectly using interactive anatomical atlas programs that map the atlas image onto the stereotactic image of the brain. As is described in greater detail below, the anatomical targets may be stimulated directly or affected through stimulation in another region of the brain.

Based upon the coordinates derived from the procedure above, the electrical stimulation lead can be positioned in the brain. Typically, an insertion cannula for electrical stimulation lead is inserted through the burr hole into the brain, but a cannula is not required. For example, a hollow needle may provide the cannula. The cannula and electrical stimulation lead may be inserted together or lead may be inserted through the cannula after the cannula has been inserted.

Once an electrical stimulation lead has been positioned in the brain, the lead is uncoupled from any stereotactic equipment present, and the cannula and stereotactic equipment are removed. Where stereotactic equipment is used, the cannula may be removed before, during, or after removal of the stereotactic equipment. Where appropriate, any burr hole cover seated in the burr hole may be used to secure electrical stimulation lead 64 in position and possibly to help prevent leakage from the burr hole and entry of contaminants into the burr hole. Example burr hole covers that may be appropriate in certain embodiments are illustrated and described in co-pending U.S. Application Nos. 60/528,604 and 60/528,689, both filed Dec. 11, 2003 and entitled "Electrical Stimulation System and Associated Apparatus for Securing an Electrical Stimulation Lead in Position in a Person's Brain", each of which are incorporated herein in its entirety.

Once electrical stimulation lead has been inserted and secured, connecting portion lead extends from the lead insertion site to the implant site at which stimulation source is implanted. The implant site is typically a subcutaneous pocket formed to receive and house stimulation source. The implant site is usually positioned a distance away from the insertion site, such as near the chest, below the clavicle or alternatively near the buttocks or another place in the torso area. Once all appropriate components of stimulation system are implanted, these components may be subject to mechanical forces and movement in response to movement of the person's body. A doctor, the patient, or another user of stimulation source may directly or indirectly input signal parameters for controlling the nature of the electrical stimulation provided.

Although example processes are illustrated and described, the present invention contemplates two or more processes taking place substantially simultaneously or in a different order. In addition, the present invention contemplates using methods with additional processes, fewer processes, or different processes, so long as the processes remain appropriate for implanting an example stimulation system into a person for electrical stimulation of the person's brain.

According to one embodiment of the present invention, the predetermined site, such as the amygdalohippocampal complex, is stimulated using stimulation parameters such as, pulse width of about 1 to about 500 microseconds, more preferable, about 1 to about 90 microseconds; frequency of about 1 to about 300 Hz, more preferably, about 100 to about 185 Hz; and voltage of about 0.5 to about 10 volts, more preferably about 1 to about 10 volts. It is known in the art that the range for the stimulation parameters may be greater or smaller depending on the particular patient needs and can be determined by the physician. Other parameters that can be considered may include the type of stimulation for example, but not limited to acute stimulation, subacute stimulation, and/or chronic stimulation.

The stimulation system of the present invention is surgically implanted as described in the above sections. One of skill in the art is cognizant that a variety of electrodes or electrical stimulation leads may be utilized in the present invention. It is desirable to use an electrode or lead that contacts or conforms to the target site for optimal delivery of electrical stimulation. One such example, is a single multi contact electrode with eight contacts separated by 2½ mm, and each contract would have a span of approximately 2 mm. Another example is an electrode with two 1 cm contacts with a 2 mm intervening gap. Yet further, another example of an electrode that can be used in the present invention is a 2 or 3 branched electrode/catheter to cover the predetermined site or target site. Each one of these three pronged catheters/electrodes have four contacts 1-2 mm contacts with a center to center separation of 2 of 2.5 mm and a span of 1.5 mm. Similar designs with catheters to infuse drugs with single outlet pore at the extremities of these types of catheters or along their shaft may also be designed and used in the present invention.

Figure 4:
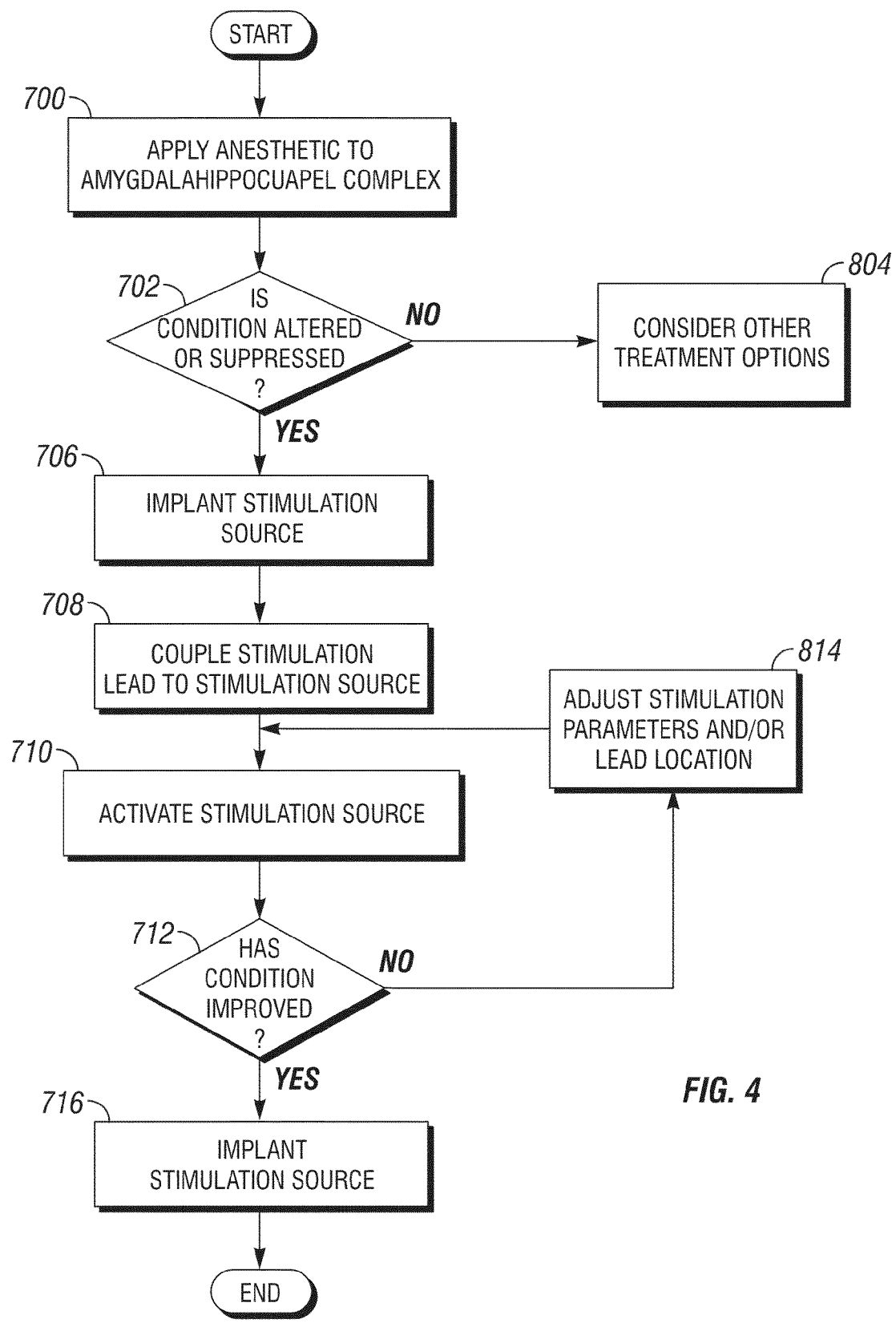
FIG. 4 is a block diagram of processes according to a method for treating auditory dysfunction using a stimulation system.

FIG. 4 illustrates an example method of treating a neurological condition or disorder using stimulation system 10, described in FIG. 1 above, implanted into a person's body with stimulation lead 14 located in communication with a predetermined brain region. In a preferred embodiment, the predetermined brain region is the amygdalohippocampal complex.

At process 700, an anesthetic stimulation agent is applied to the amygdalohippocampal complex (AHC) via selective anterior choroidal artery catherization. Process 700 is performed to test if the AHC is likely to be involved as the source of any tinnitus experienced by the patient. In one procedure used with certain embodiments of the invention, 80 mg amobarbital is injected on one side of the body and the patient's tinnitus is evaluated. The AHC on the other hemisphere is treated after the effects of the amobarbital subside, usually after about 10 minutes. The time between treatments will vary if other stimulation agents are used or if different dosages of amobarbital are used. Individual variations are also encountered. Note that certain embodiments do not use the test procedure of process 700.

In process 702, a patient's neurological condition or disorder is evaluated. Evaluation comprises formal subjective questioning of the person, formal subjective testing and analysis according to one or more neurological test described below. Other analyses may also be performed to determine whether the subject's condition has sufficiently improved through the intra-implantation trial stimulation. If neurological condition has not improved, other treatment options may be considered in process 704.

At process 706, one or more stimulation leads 14 are implanted such that one or more stimulation electrodes 18 of each stimulation lead 14 are positioned in communication with a predetermined brain region (for the purposes described herein and as those skilled in the art will recognize, when an embedded stimulation system, such as the Bion®, is used, it is positioned similar to positioning the lead 14). Techniques for implanting stimulation leads such as stimulation lead 14 are known to those skilled in the art and described in detail above. In certain embodiments, as described above, one or more stimulation electrodes 18 are positioned in communication with a predetermined brain region. The electrodes are carried by percutaneous leads, which commonly have two or more, equally-spaced electrodes, and are placed subcutaneously in communication with the predetermined brain region.

At process 708, if necessary, stimulation source 12 may be coupled directly to connecting portion 16 of stimulation lead 14. Alternatively, as described above and if necessary, stimulation source 12 may not be coupled directly to stimulation lead 14 and may instead be coupled to stimulation lead 14 via an appropriate wireless link. Of course, as those skilled in the art know, an embedded stimulation system will not need to be so coupled.

Intra-implantation trial stimulation may be conducted at processes 710 through 713. At process 710, stimulation source 12 is activated to generate and transmit stimulation pulses via one or more stimulation electrodes 18. At process 712, informal subjective questioning of the person, formal subjective testing and analysis according to one or more neurological tests and/or other analyses may be performed to determine whether the subject's condition has sufficiently improved through the intra-implantation trial stimulation. If the subject's condition has not sufficiently improved, one or more stimulation parameters may be adjusted, stimulation lead 14 may be moved incrementally or even re-implanted, or both of these modifications may be made at process 714 and the trial stimulation and analysis repeated until the condition has sufficiently improved. Once the stimulation parameters have been properly set and stimulation lead 14 has been properly positioned such that subject's condition has improved, intra-implantation trial stimulation is complete. One of skill in the art is aware that other types of intra-implantation trailing methods or stimulation trails can be used in the present invention, for example, but not limited to transcutaneous electrical nerve stimulation (TENS), trans-magnetic stimulation (TMS), nerve blocks, etc.

Once stimulation lead 14 has been properly implanted and secured, and any trial stimulation completed, if necessary, stimulation source 12 is implanted at process 716. Techniques for implanting stimulation sources such as stimulation source 12 are known to those skilled in the art. For non-embedded systems, the implant site is typically a subcutaneous pocket formed to receive and house stimulation source 12. The implant site is usually located some distance away from the insertion site, such as in or near the upper back or shoulders. Where stimulation lead 14 includes connecting portion 16, connecting portion 16 may be tunneled, at least in part, subcutaneously to the implant site of stimulation source 12. Some embodiments of the invention may use a non-implantable stimulation source. In certain embodiments a doctor, the patient, or another user of stimulation source 12 may directly or indirectly input stimulation parameters for controlling the nature of the electrical stimulation provided to the predetermined brain region, if not already set during any intra-implantation trial stimulation period. Where appropriate, post-implantation trial stimulation may be conducted, over one or more weeks or months for example, and any necessary modifications made accordingly.

Although example processes are illustrated and described, the present invention contemplates two or more processes taking place substantially simultaneously or in a different order. In addition, the present invention contemplates using methods with additional processes, fewer processes, or different processes, so long as the processes remain appropriate for implanting stimulation system 10 into a person for electrical stimulation of the predetermined site, such as, for example the AHC.

IV. Infusion Pumps

In further embodiments, it may be desirable to use a drug delivery system independently or in combination with electrical stimulation to result in the stimulation parameters of the present invention. Drug delivery may be used independent of or in combination with a lead/electrode to provide electrical stimulation and chemical stimulation. When used, the drug delivery catheter is implanted such that the proximal end of the catheter is coupled to a pump and a discharge portion for infusing a dosage of a pharmaceutical or drug. Implantation of the catheter can be achieved by combining data from a number of sources including CT, MRI or conventional and/or magnetic resonance angiography into the stereotactic targeting model. Thus, implantation of the catheter can be achieved using similar techniques as discussed above for implantation of electrical leads, which is incorporated herein. The distal portion of the catheter can have multiple orifices to maximize delivery of the pharmaceutical while minimizing mechanical occlusion. The proximal portion of the catheter can be connected directly to a pump or via a metal, plastic, or other hollow connector, to an extending catheter.

Any type of infusion pump can be used in the present invention. For example, "active pumping" devices or so-called peristaltic pumps are described in U.S. Pat. Nos. 4,692,147, 5,840,069, and 6,036,459, which are incorporated herein by reference in their entirety. Peristaltic pumps are used to provide a metered amount of a drug in response to an electronic pulse generated by control circuitry associated within the device. An example of a commercially available peristaltic pump is SynchroMed® implantable pump from Medtronic, Inc., Minneapolis, Minn.

Other pumps that may be used in the present invention include accumulator-type pumps, for example certain external infusion pumps from Minimed, Inc., Northridge, Calif. and Infusaid® implantable pump from Strato/Infusaid, Inc., Norwood, Mass. Passive pumping mechanisms can be used to release an agent in a constant flow or intermittently or in a bolus release. Passive type pumps include, for example, but are not limited to gas-driven pumps described in U.S. Pat. Nos. 3,731,681 and 3,951,147; and drive-spring diaphragm pumps described in U.S. Pat. Nos. 4,772,263, 6,666,845, 6,620,151 all of which are incorporated by reference in their entirety. Pumps of this type are commercially available, for example, Model 3000® from Arrow International, Reading, Pa. and IsoMed® from Medtronic, Inc., Minneapolis, Minn.; AccuRx® pump from Advanced Neuromodulation Systems, Inc., Plano, Tex.

In certain embodiments, the catheter can be in the form of a lead catheter combination, similar to the ones described in U.S. Pat. No. 6,176,242 and U.S. Pat. No. 5,423,877, which are incorporated herein by reference in their entirety.

Still further, the present invention can comprise a chemical stimulation system that comprises a system to control release of neurotransmitters (e.g., glutamate, acetylcholine, norepinephrine, epinephrine), chemicals (e.g., zinc, magnesium, lithium) and/or pharmaceuticals that are known to alter the activity of neuronal tissue. For example, infusion formulation delivery system can utilize a control system having an input-response relationship. A sensor generates a sensor signal representative of a system parameter input (such as levels of neurotransmitters), and provides the sensor signal to a controller. The controller receives the sensor signal and generates commands that are communicated to the infusion formulation delivery device. The infusion formulation delivery device then delivers the infusion formulation output to the predetermined site at a determined rate and amount in order to control the system parameter.

Sensor may comprise a sensor, sensor electrical components for providing power to the sensor and generating the sensor signal, a sensor communication system for carrying the sensor signal to controller, and a sensor housing for enclosing the electrical components and the communication system. Controller may include one or more programmable processors, logic circuits, or other hardware, firmware or software components configured for implementing the control functions described herein, a controller communication system for receiving the sensor signal from the sensor, and a controller housing for enclosing the controller communication system and the one or more programmable processors, logic circuits, or other hardware, firmware or software components. The infusion formulation delivery device may include a suitable infusion pump, infusion pump electrical components for powering and activating the infusion pump, an infusion pump communication system for receiving commands from the controller, and an infusion pump housing for enclosing the infusion pump, infusion pump electrical components, and infusion pump communication system. Such systems are described in U.S. Pat. No. 6,740,072, which is incorporated herein by reference in its entirety.

In certain embodiments, the sensor can be an electrode that senses a hyperactive burst pattern of activity, which in turns stimulates the infusion pump to release a chemical or stimulating drug or agent to modify the neuronal activity. The chemical or stimulating agent can be either an inhibiting agent or stimulating agent.

Herein, stimulating drugs comprise medications, anesthetic agents, synthetic or natural peptides or hormones, neurotransmitters, cytokines and other intracellular and intercellular chemical signals and messengers, other agents such as zinc and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

Similarly, excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., flouxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxasid)), generally have an excitatory effect on neural tissue, while inhibitory neurotransmitters (e.g., dopamine, glycine, and gamma-aminobutyric acid (GABA)), agonists thereof, and agents that act to increase levels of an inhibitory neurotransmitter(s) generally have an inhibitory effect (e.g., benzodiasepine (e.g., chlordiazepoxide, clonazepam, diazepam, lorazepam, oxazepam, prazepam alprazolam); flurazepam, temazepam, or triazolam). (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., prazosin, and metoprolol) and agents that decrease levels of excitatory neurotransmitters may inhibit neural activity. Yet further, lithium salts, anesthetics (e.g., lidocane), and magnesium may also be used in combination with electrical stimulation.

V. Treating Neurological Conditions

The present stimulation system and/or method acts to stimulate neuronal tissue which in turn stimulate the brain and cause/allow the brain to act in the best interest of the host through use of the brain's natural mechanisms. Until know, one of skill in the art has failed to recognize that stimulation of the amygdalohippocampal complex as described in the present invention can provide the therapeutic treatments according to the instant invention. Yet further, stimulation of other components of the limbic system can also be stimulated in the present invention, for example, parahippocampus, perirhinal cortex, and entorhinal cortex.

It is known that the hippocampus functions as a comparator, comparing internal (phantom phenomena and cognitive stimuli such as thoughts, emotions, autonomic stimuli) and external sensory (auditory, visual, olfactory, visual, somatosensory) stimuli to what is stored in memory, for example it decides if the incoming stimulus or signal is novel. The amygdala is a relevance detector, for example, it verifies whether the emotional system, which is a priority mode inducing system, has to be activated in order to give priority to the internal or external stimulus. One of the ways to do this is by bringing it to consciousness, which is the reason why people suffer from the stimulus.

Thus, the present invention envisions treating neurological disease by regulating or modulating the uncontrolled hyperactivity of this priority mode inducing system (amygdala+ hippocampus). For example, low frequency stimulation, may reset this hyperactivity to a normal lower pace.

Accordingly, the present invention relates to modulation of neuronal activity to affect neurological, neuropsychological or neuropsychiatric activity. The present invention finds particular application in the modulation of neuronal function or processing to affect a functional outcome. The modulation of neuronal function is particularly useful with regard to the prevention, treatment, or amelioration of neurological, psychiatric, psychological, conscious state, behavioral, mood, and thought activity (unless otherwise indicated these will be collectively referred to herein as "neurological activity" which includes "psychological activity" or "psychiatric activity"). The main clinical entities to be treated can be subdivided in three groups: hypolimbic syndromes, hyperlimbic syndromes and dysfunctional limbic syndromes. Hypolimbic syndromes comprise depression, apathy, amnesia and the Kluver-Bucy syndrome. Hyperlimbic syndromes consist of mania, obsessive compulsive disorder, limbic epilepsy and rage. Dysfunctional limbic syndromes consist of psychosis, social disdecorum, anxiety/panic disorders, utilization behavior (Cummings and Mega 2003). However it should be clear to one skilled in art that the amygdalohippocampal neuromodulation is not limited to these indications. When referring to a pathological or undesirable condition associated with the activity, reference may be made to a neurological disorder which includes "psychiatric disorder" or "psychological disorder" instead of neurological activity or psychiatric or psychological activity. Although the activity to be modulated usually manifests itself in the form of a disorder such as a attention or cognitive disorders (e.g., Autistic Spectrum Disorders); mood disorder (e.g., major depressive disorder, bipolar disorder, and dysthymic disorder) or an anxiety disorder (e.g., panic disorder, posttraumatic stress disorder, obsessive-compulsive disorder and phobic disorder); neurodegenerative diseases (e.g., multiple sclerosis, Alzheimer's disease, amyotrophic lateral sclerosis (ALS), Parkinson's disease, Huntington's Disease, Guillain-Bane syndrome, myasthenia gravis, and chronic idiopathic demyelinating disease (CID)), movement disorders (e.g, dyskinesia, tremor, dystonia, chorea and ballism, tic syndromes, Tourette's Syndrome, myoclonus, drug-induced movement disorders, Wilson's Disease, Paroxysmal Dyskinesias, Stiff Man Syndrome and Akinetic-Ridgid Syndromes and Parkinsonism), epilepsy, tinnitus, pain, phantom pain, diabetes neuropathy, one skilled in the art appreciates that the invention may also find application in conjunction with enhancing or diminishing any neurological or psychiatric function, not just an abnormality or disorder. Neurological activity that may be modulated can include, but not be limited to, normal functions such as alertness, conscious state, drive, fear, anger, anxiety, repetitive behavior, impulses, urges, obsessions, euphoria, sadness, and the fight or flight response, as well as instability, vertigo, dizziness, fatigue, photofobia, concentration dysfunction, memory disorders, headache, dizziness, irritability, fatigue, visual disturbances, sensitivity to noise (misophonia, hyperacusis, phonofobia), judgment problems, depression, symptoms of traumatic brain injury (whether physical, emotional, social or chemical), autonomic functions, which includes sympathetic and/or parasympathetic functions (e.g., control of heart rate), somatic functions, and/or enteric functions. Thus, the present invention encompasses modulation of central and/or peripheral nervous systems.

Other neurological disorders can include, but are not limited to headaches, for example, migraine, trigeminal autonomic cephalgia (cluster headache (episodic and chronic)), paroxysmal hemicrania (epidsodic and chronic), hemicrania continua, SUNCT (short-lasting unilateral neuralgiform headache with conjunctival injection and tearing), cluster tic syndrome, trigeminal neuralgia, tension type headache, idiopathic stabbing headache, etc. The neurostimulation device can be implanted intracranially or peripherally, for example, but not limited to implanting a neurostimulation device occipitally or hypothalamically for the treatment of headaches. Via its autonomic effects, the amygdalohippocampal stimulation is capable of modifying headaches, especially but not limited to trigeminal autonomic cephalgia.

Autonomic and/or enteric nervous system disorders that can be treated using the stimulation system and/or method of the present invention include, but are not limited to hypertension, neurosis cordis or heart rhythm disorders, obesity, gastrointestinal motion disorders, respiratory disorders, diabetes, sleep disorders, snoring, incontinence both urologic and gastrointestinal, sexual dysfunction, chronic fatigue syndrome, fibromyalgia, whiplash associated symptoms, post-concussion syndrome, posttraumatic stress disorder etc. The central autonomic network (CAN) is an integral component of an internal regulation system through which the brain controls visceromotor, neuroendocrine, pain, and behavioral responses essential for survival. It includes the insular cortex, amygdala, hypothalamus, periaqueductal gray matter, parabrachial complex, nucleus of the tractus solitarius, and ventrolateral medulla. The CAN controls preganglionic sympathetic and parasympathetic, neuroendocrine, respiratory, and sphincter motoneurons. The insular cortex and amygdala mediate high-order autonomic control, and their involvement in seizures or stroke may produce severe cardiac arrhythmias and other autonomic manifestations (Benarroch 1993). Electrical stimulation of the amygdala activates catecholamine producing cells in the ventrolateral medulla oblongata and the nucleus tractus solitarius (Petrov, Jhamandas et al. 1996), control centra of sympathetic and parasympathetic regulation respectively, and the central nucleus of the amygdala is involved in the parasympathetic outflow during stress (Roozendaal, Koolhaas et al. 1991). As such, amygdalohippocampal stimulation can modify the autonomic nervous system and treat pathologies or clinical conditions associated with a dysregulation of the sympathetic and parasympathetic system.

Yet further immunological disorders may also be treated using the stimulation system and/or method of the present invention. An interrelationship between the medial septum and the hippocampal formation, bed nucleus of the stria terminalis, the medial amygdala, and the hypothalamus (both medial and lateral) as a possible circuit involved in the regulation of cellular immune functions has been demonstrated (Jurkowski, Trojniar et al. 2001). It has also been shown that the amygdala can strongly influence subsequent responsiveness to a repeated stress, mediated in part by both CRF and GABA actions, and hypersecretion of CRF in the brain may contribute to the symptomatology seen in neuropsychiatric disorders, such as depression, anxiety-related disorders and anorexia nervosa. Furthermore, overproduction of CRF at peripheral inflammatory sites, such as synovial joints may contribute to autoimmune diseases such as rheumatoid arthritis. In contrast, deficits in brain CRF are apparent in neurodegenerative disorders, such as Alzheimer's disease, Parkinson's disease and Huntington's disease, as they relate to dysfunction of CRF neurons in the brain areas affected in the particular disorder (De Souza 1995). Electrical stimulation in all of the limbic regions leads to elevated plasma corticosterone levels (Feldman, Siegel et al. 1983). This is based on the fact that the immune system senses antigens coordinates metabolic, endocrine and behavioral changes that support the immune system and modulates the immune system via neuroendocrine regulation and direct immune cell regulation. The amygdalohippocampal stimulation has its influence on immunological disorders via the neuroendocrine axis (hypothalamo-pituitary-adrenal axis). Such immunological disorders include, such as allergy, rhinitis, asthma, rheumatoid arthritis, psoriasis arthritis, lupus ereythematosus disseminatus, multiple sclerosis and other demyelinating disorders, autoimmune thyroiditis, Crohn's disease, diabetis melitus etc. In addition to immunological disorders, it is envisioned that sepsis can also be treated using the stimulation system of the present invention.

Yet further tumoral disorders, both malignant and benign may also be treated using the stimulation system and/or method of the present invention. This is based on the fact that tumoral behavior is linked to immunological function. This is seen in immunodeficiency syndromes such as AIDS and hematological disorders, where multiple and different tumors develop. In this setting neuromodulation could indirectly influence tumoral behavior.

Yet further neuroendocrine disorders may also be treated using the stimulation system and/or method of the present invention. Such disorders are stress reactions, hypothalamic-pituitary axis dysfunction, etc.

Yet further functional disorders may also be treated using the stimulation system and/or method of the present invention. Such disorders can be anorexia, boulemia, addictions, phobias, psychosis, depression, bipolar disorder, kleptomania, aggression, paraphilia or antisocial sexual behavior. One skilled in the art appreciates that the invention may also find application in conjunction with enhancing or diminishing any neurological or psychiatric function, not just an abnormality or disorder.

The present invention is particularly useful in the treatment of neurological conditions and/or disorders in humans. However, one skilled in the art appreciates that the present invention is applicable to other animals which experience neurological conditions and/or disorders. This may include, for example, primates, canines, felines, horses, elephants, dolphins, etc. Utilizing the various embodiments of the present invention, one skilled in the art may be able to modulate the amygdalohippocampal complex via brain region stimulation to achieve a desirable result.

One technique that offers the ability to affect neuronal function is the delivery of electrical and/or chemical and/or magnetic and/or thermal and/or ultrasound stimulation for neuromodulation directly to target tissues or predetermined neuronal sites via an implanted device having a probe. The probe can be stimulation lead or electrode assembly. The electrode assembly may be one electrode, multiple electrodes, or an array of electrodes in or around the target area. The proximal end of the probe is coupled to a system to operate the device to stimulate the target site. Thus, the probe is coupled to an electrical signal source, which, in turn, is operated to stimulate the target tissue or predetermined site.

A probe is implanted in communication with a predetermined site. The predetermined site can be selected from the group consisting of amygdala, hippocampus, parahippocampus, perirhinal cortex, and entorhinal cortex, and any projections associated therewith. Still further, the predetermined site is the amygdalohippocampal comlex which comprises the brain tissue or regions associated with the amygdala and/or the hippocampus and the projections thereof. It is known that the amygdala comprises efferent (descending) projections or pathways, for example, stria terminalis and the ventral amygdalofugal pathway. The stria terminalis pathway innervates the bed neucleus of the stria terminalis, the nucleus accumbens, and the hypothalamus. The ventral amygdalofugal pathway provides input to the hypothalamus, dorsal medial nucleus of the thalamus, and the rostral cingulate gyms. Yet further, the amygdala receives afferent (ascending) input from the olfactory system and also the cerebral cortex (limbic and sensory association cortices) and the hypothalamus. Outputs or the efferent pathway of the hippocampus from Ammon's horn and the subiculum. It is known by those of skill in the art that fibers from the subiculum terminate directly in the basal and lateral nuclei of the amygdala, entorhinal cortex (parahippocampal gyms area), retrosplenial cortex and via the cingulum, the cingulate cortex. Thus, one of skill in the art realizes that stimulation of the amygdalohippocampal complex includes not only the identified structures associated therewith, but also the projections associated therewith. Thus, the present invention includes stimulating the structures or projections that result in a modulation of neural activity of the amygdalohippocampal complex, such that a neurological condition or disorder is treated or affected.

Using the stimulation system of the present invention, the predetermined site or target area is stimulated in an effective amount or effective treatment regimen to decrease, reduce, modulate or abrogate the neurological disorder. Thus, a subject is administered a therapeutically effective stimulation so that the subject has an improvement in the parameters relating to the neurological disorder or condition including subjective measures such as, for example, neurological examinations and neuropsychological tests (e.g., Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, MADRAS, CGI, N-BAC, or Yale-Brown Obsessive Compulsive score (Y-BOCS)), motor examination, and cranial nerve examination, and objective measures including use of additional psychiatric medications, such as anti-depressants, or other alterations in cerebral blood flow or metabolism and/or neurochemistry.

Patient outcomes may also be tested by health-related quality of life (HRQL) measures: Patient outcome measures that extend beyond traditional measures of mortality and morbidity, to include such dimensions as physiology, function, social activity, cognition, emotion, sleep and rest, energy and vitality, health perception, and general life satisfaction. (Some of these are also known as health status, functional status, or quality of life measures.)

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known subject's history.

For purposes of this invention, beneficial or desired clinical results include, but are not limited to, alleviation of symptoms, improvement of symptoms, diminishment of extent of disease, stabilized (i.e., not worsening) state of disease, delay or slowing of disease progression, amelioration or palliation of the disease state, and remission (whether partial or total), whether objective or subjective. The improvement is any observable or measurable improvement. Thus, one of skill in the art realizes that a treatment may improve the patient condition, but may not be a complete cure of the disease.

In certain embodiments, in connection with improvement in one or more of the above or other neurological disorders, the electrical stimulation may have a "brightening" effect on the person such that the person looks better, feels better, moves better, thinks better, and otherwise experiences an overall improvement in quality of life.

One example of stimulation parameters used to treat neurological conditions uses an amplitude in the range of about 2 mA to about 100 mA, a frequency in the range of about 3 Hz to about 50 Hz, and a pulse width in the range of about 5 microseconds to about 100 microseconds. As noted above, this is an exemplary set of stimulation parameters. Embodiments of the invention contemplate adjusting stimulation parameters to optimize treatment for each individual, and the stimulation parameters accordingly vary depending on the neurological condition and/or disorder, and a multitude of other factors.

One of skill in the art is aware that stimulation parameters can be varied to achieve the desired result. One such parameter that may be varied in the present invention is signal frequency. Altering the frequency signal can result in the generation of a bursting type rhythm or burst stimulus frequency or burst mode stimulation, as Burst mode stimulation may also be used as described above and in U.S. application "New Stimulation Design for Neuromodulation", filed Oct. 20, 2005 incorporated by reference herein.

In certain embodiments, the burst stimulus frequency may be in the range of about 1 Hz to about 100 Hz, more particular, in the range of about 1 Hz to about 12 Hz, and more particularly, in the range of about 1 Hz to about 4 Hz, 4 Hz to about 7 Hz or about 8 Hz to about 12 Hz for each burst. One skilled in the art will further realize that each burst stimulus comprises at least two spikes, for example, each burst stimulus can comprise about 12 to about 100 spikes, more particularly, about 2 to about 10 spikes. Each spike can comprise a frequency in the range of about 50 Hz to about 1000 Hz, more particularly, in the range of about 200 Hz to about 500 Hz. One of skill in the art is aware that the frequency for each spike within a burst can be variable, thus it is not necessary for each spike to contain similar frequencies, e.g., the frequencies can vary in each spike. The inter-spike interval can be also vary, for example, the inter-spike interval, can be about 0.5 milliseconds to about 100 milliseconds or any range therebetween. The burst stimulus is followed by an inter-burst interval a duration in the range of about 5 milliseconds to about 5 seconds, more preferably, about 10 milliseconds to about 300 milliseconds. It is envisioned that the burst stimulus has a duration in the range of about 10 milliseconds to about 5 seconds, more particular, in the range of about 250 msec to 1000 msec (1-4 Hz burst firing), 145 msec to about 250 msec (4-7 Hz,), 145 msec to about 80 msec (8-12 Hz) or 1 to 5 seconds in plateau potential firing. The burst stimulus and the inter-burst interval can have a regular pattern or an irregular pattern (e.g., random or irregular harmonics).

In further embodiments, the stimulation system of the present invention can incorporate an infusion or drug delivery device. The device can contain a sensor, for example an electrode, that senses a hyperactive burst pattern of activity, which in turns stimulates the infusion pump to release a chemical or stimulating drug or agent to modify the neuronal activity. The chemical or stimulating agent can be either an inhibiting agent or stimulating agent, as described above.

In addition to electrical stimulation and/or chemical stimulation, other forms of stimulation can be used, for example magnetic, or thermal or combinations thereof. Magnetic stimulation can be provided by internally implanted probes or by externally applied directed magnetic fields, for example, U.S. Pat. Nos. 6,592,509; 6,132,361; 5,752,911; and 6,425,852, each of which is incorporated herein in its entirety. Thermal stimulation can be provided by using implanted probes that are regulated for heat and/or cold temperatures which can stimulate or inhibit neuronal activity, for example, U.S. Pat. No. 6,567,696, which is incorporated herein by reference in its entirety. Still further, stimulation may also be in the form of ultrasound. (Norton 2003).

A. Deafferentation Disorders: Tinnitus and Phantom Pain.

The auditory system comprises components that convert sound pressure waves into neural impulses that are ultimately processed by the nervous system. The auditory canal channels pressure waves to tympanic membrane which moves in response to incoming waves. Movement of the tympanic membrane is transmitted to three ossicles located in the middle ear. The ossicles amplify the movement of the tympanic membrane so that sound vibrations are converted to high pressure sound waves in fluid located in the cochlea. The cochlea is divided into two fluid-filled chambers separated by the organ of Corti. Vibrations in the fluid cause mechanical stimulation of sensory receptor cells known as hair cells on the organ of Corti. This mechanical stimulation causes ion channels on the hair cells to open, altering their membrane potential and changing the release rate of a synaptic neurotransmitter. Afferent nerve fibers from the auditory nerve take up the neurotransmitter and an action potential in the nerve fibers may be generated depending on the quantity of released neurotransmitter.

The auditory nerve connects to two separate pathways after leaving the cochlea. The lemniscal pathway, also known as the classical or specific auditory pathway, is the route taken for signals that humans consciously perceive as sound information. The lemniscal is phylogenetically the youngest of the two pathways. The lemniscal pathway is organized tonotopically, with specific parts of the pathway carrying information specific to received auditory frequencies. It is also linear, such that the impulse rate of lemniscal neurons is related to the amplitude of sound waves detected at the cochlea.

The lemniscal pathway is generally described as axons carrying impulses from the cochlea connect to the inferior colliculus and the medial geniculate body in the thalamus to the auditory cortex. Specifically, primary axons in synaptic contact with the hair cells of the organ of Corti have their cell bodies in the spiral ganglion and enter the brainstem at the juncture of the pons and cerebellum. Here, each axon bifurcates and synapses in the dorsal and ventral cochlear nuclei of the medulla. Second order axons from the dorsal and ventral cochlear nuclei may synapse in the superior olive or may pass directly to the nucleus of the inferior colliculus via the lateral leminiscus. These connections may be made both ipsilaterally and contralaterally.

The second pathway connected to by the auditory nerve is the extralemniscal pathway. This pathway is also known as the non-classical, nonspecific, polysensory, or diffuse auditory pathway, and is used for autonomous reactions to auditory stimuli. Moller and Rollins have found evidence suggesting that this pathway may also be used for conscious hearing in children. The extralemniscal pathway is phylogenetically older than the lemniscal system. Because it is used for autonomous reactions, it is a faster transmission path and is also non-tonotopic and non-linear. Cells of the extralemniscal pathway fire in burst mode and have a slow spontaneous firing rate relative to the lemniscal pathway cells. The auditory extralemniscal pathway makes connections with the somatosensory system at the dorsal cochlear nucleus and the inferior colliculus. Extralemniscal connections at the inferior colliculus 201 occur at the external nucleus and the dorsal cortex. These ascending pathways then connect at all divisions of the medial geniculate bodies, the posterior intralaminar complex, and suprageniculate nuclei at the level of the superior colliculus. Afferent dorsal column neurons connect with the extralemniscal pathway at the external nucleus and the dorsal cortex. Afferent projections from the thalamus and the medial geniculate bodies to the amygdala are present. The amygdala also receives projections from the auditory cortex.

There are also connections between the trigeminal system and the ventral cochlear nucleus. The dorsal cochlear nucleus receives input from the dorsal column (proprioception) nuclei and the ventral cochlear nucleus from the trigeminal ganglion (Shore, Vass et al. 2000; Shore, El Kashlan et al. 2003; Weinberg and Rustioni 1987). The trigeminal ganglion also connects to the superior olivary nucleus (Shore, Vass et al. 2000). Electrical stimulation of the somatosensory trigeminal ganglion can influence the activity of central auditory neurons in a manner distinct from acoustic stimulation, suggesting activation of non-classical auditory pathways (El-Kashlan and Shore 2004). Furthermore, the activation seems to be predominantly ipsilateral (El-Kashlan and Shore 2004). These connections may be involved in generating or modulating perceptions of phantom sounds which can be modified by manipulations of somatic regions of the head and neck ("somatic tinnitus")(Levine, Abel et al. 2003; Shore, El Kashlan et al. 2003). Also, C2 (occipital and greater auricular nerve) innervates the dorsal cochlear nucleus (Kanold and Young 2001) as well as the rest of the body via the cuneate nucleus of the dorsal column (Itoh, Kamiya et al. 1987; Wright and Ryugo 1996).

Amygdalohippocampal stimulation is used in certain embodiments of the present invention to treat auditory dysfunction. Amygdalohippocampal stimulation targets two different systems; the limbic system and the memory system.

The limbic system is targeted by stimulation of the amygdala because of connections made through this component. Auditory information can reach the amygdala by two routes: 1) a fast route via direct connections between the dorsal and medial part of the MGB (non classical thalamus), and 2) the lateral nucleus of the amygdala also known as the low route and slower phylogenetically more recent route passing via the cortex. The low route carries information from the non-classical auditory pathway, while the high route carries information from classical auditory pathways (LeDoux 1996; Moller 2000). The information from the two routes becomes integrated in the lateral nucleus of the amygdala. It does so by using two different glutamate receptors, fast AMPA receptors and slow NMDA receptors. The slow route uses only AMPA receptors and the fast route uses both slow NMDA and fast AMPA receptors (Li, Phillips et al. 1995; Li, Stutzmann et al. 1996). The NMDA receptors of the low route exhibit symptomatic plasticity, as demonstrated by the presence of LTP, which may underlie emotional learning (LeDoux 1993) such as unconscious fear conditioning (which can be considered an emotional Pavlov reflex, associating fear reactions to a neutral tone). If a person is surprised by an auditory stimulus, the amygdala reacts quickly if the noise is unexpected. As an example of the information routing, consider the following example. A person walking in the woods hears a loud unexpected crackling sound. Perception of the sound goes straight to the amygdala via the low route and to the cortex via the high route. The amygdala recognizes the crackling sound (which could be a rattle snake shaking its tail or a dry twig snapping under the weight of the person's boot) and reacts blindly by withdrawing the person's foot instantaneously. By that time the cortex has figured out whether the noise is that of a snake or a twig, and it will make the amygdala react appropriately, either by slowing down the likely running-away movement or enhancing the precautionary response (LeDoux 1996, p. 163). In other words, the cortex acts to prevent inappropriate reactions rather than to produce appropriate ones.

Thus, the amygdala produces conscious and unconscious fear responses to auditory (and other sensory) stimuli. The amygdala has many connections to the hypothalamus (controlling activation of the sympathetic nervous system), the pituitary (controlling stress hormone release), and to the brainstem where avoidance behaviour is regulated in the peri aquaductal grey matter. Activation of amygdala connections to motor neurons and the anatomic system result in increasing vigilance and muscle tension. The amygdala also has connections to the thalamus, hippocampus, prefrontal cortex, basal forebrain and anterior cingulate cortex. Interestingly, the projections of the amygdala to the cortex are 10 times greater than the projections from the cortex to the amygdala (LeDoux 1996)

As mentioned above, amygdalohippocampal stimulation targets two different systems: the limbic system and the memory system. The memory system can be subdivided in two parallel systems, one conscious and one unconscious. The conscious system is also known as declarative or explicit memory, and the unconscious system is also known as non-declarative or implicit memory. Conscious memory is mediated via the hippocampus and diencephalon, and the unconscious probably via the cerebellum, vermis and basal ganglia and amygdala (LeDoux 1996; Squire and Kandel 2000; Bear, Connors et al. 2001). The auditory cortex itself is also capable of storing non-conscious short and long-term auditory memory traces (Weinberger 2004).

The connections of conscious memory derive from the association areas and reach the hippocampus via the parahippocampal, perirhinal and entorhinal cortex. From the entorhinal cortex the medial and lateral perforant pathway lead to the hippocampus. The efferent pathway from the hippocampus is mainly via the fornix to the hypothalamus (Purves, Augustine et al. 1997; Rosenzweig, Leiman et al. 1999; Bear, Connors et al. 2001). This last pathway is responsible for conscious (explicit) memory (LeDoux 1996). The auditory cortex connects to the entorhinal area, the origin of the perforant pathways and the entry into the hippocampus (Swanson and Kohler 1986).

Unconscious, or implicit memory probably has to be subdivided in multiple subsystems. Motor implicit memory, which is regulated by the basal ganglia and cerebellum (simple reflex), simple implicit memory, which is regulated by the thalamus, and emotional implicit memory which is regulated by the amygdala (LeDoux 1996). All the structures involved in implicit memory are phylogenetically older than those involved in explicit memory Thus, auditory sensory information passes through the thalamus and from the thalamus to the amygdala, further connecting via the amygdala to the hippocampus. This can be considered the low route of memory subserving implicit memory. The same auditory information passes via the thalamus to the cortex and from there via the rhinal cortex to the hippocampus to become conscious memory. This model can explain why hippocampal lesions only lead to a loss of conscious memory while implicit memory (unconscious and routine actions) can still be learned. It also explains why thalamic lesions can lead to loss of both implicit and explicit memory, a syndrome known as thalamic or diencephalic amnesia (Ohye 2002), and why lesions of the basal ganglia can only impair implicit but not explicit memory (Pascual-Leone, Grafman et al. 1994) (Hay, Moscovitch et al. 2002). Similarly, lesions to the cerebellum can impair motor implicit memory as demonstrated by Thompson and Krupa 1994. It should however be clear that implicit and explicit memory should, at a certain stage, be integrated. An emotional situation activates the amygdala system and hippocampal system in parallel. The unconscious emotional memory processed in the amygdala and hippocampal are dependent upon conscious memory of the emotional situation to become integrated, resulting in an immediate conscious experience. This occurs in what is called working memory (LeDoux 1996). Working memory involves the temporary storage and manipulation of information that is assumed to be necessary for a wide range of complex cognitive activities. It can be divided into 4 subsystems. The first is the phonological loop, concerned with verbal and acoustic information; the second is the visuospatial sketchpad, which provides the visual equivalent of the phonological loop. Both of these are dependent upon a third attentionally-limited control system, the central executive system. A fourth subsystem is the episodic buffer (Baddeley 2003; Baddeley 2003). PET studies in humans (Grasby, Frith et al. 1993; Shallice, Fletcher et al. 1994; Fletcher, Frith et al. 1995) have demonstrated involvement of both these systems in auditory-verbal memory showing increased blood flow in the thalamus, right parahippocampal gyms, anterior cingulate, superior temporal gyms and cerebellum.

The amygdala is located anterior of the hippocampus, and is almond-shaped. Neurons located in the dorsal subdivision of the lateral amygdala respond to both auditory and somatosensory stimuli. Auditory dysfunctions such as tinnitus have been proposed to be stored in memory in the amygdalohippocampal complex (Mirz et al.). Connections from the somatosensory system to the auditory system have been explored in the past. Information from the different sensory modalities (sight, hearing, touch, etc.) is known to integrate in most higher organisms, and occurs in the human nervous system. Co-existing cutaneous and auditory responses in neuronal tissue have been observed in the caudomedial auditory cortex, adjacent to the primary auditory cortex (Fu et al., Foxe et al.). The amygdala has been linked to tinnitus in recent research studies, and possibly functions to assign emotional responses to stimuli, including presumably auditory stimuli. (Wallhausser-Franke et al.). Increases in c-fos expression in the auditory cortex have been reported in experiments where tinnitus is induced by intense sound, and recent research extends the findings to include increases in such expression in the amygdala (Zhang et al.).

Afferent neurons from the cochlea connect with the inferior colliculus which then project to the thalamus. The thalamus projects to both the auditory cortex and the amygdala, among other connections. Finally, the auditory cortex projects afferent neurons to the amygdala.

Functionally distinct prefrontal cortices receive projections from different components of the hippocampal region. Projection of neurons from the hippocampal formation innervate predominantly the medial frontal cortex and to a lesser degree the orbital prefrontal areas (Barbas and Blatt 1995), the opposite from what is known for the amygdala (Barbas and De Olmos 1990).

One technique that offers the ability to affect neuronal function is the delivery of electrical or chemical stimulation for neuromodulation directly to target tissues via an implanted device having a probe. The probe can be a stimulation lead or electrode assembly. The electrode assembly may be one electrode, multiple electrodes, or an array of electrodes in or around the target area. The proximal end of the probe is coupled to system to operate the device to stimulate the target site. Thus, the probe is coupled to an electrical signal source, which, in turn, is operated to stimulate the predetermined treatment site of a brain region. In the case of unilateral auditory dysfunction, contralateral brain region stimulation may be more effective than ipsilateral stimulation. However, as the auditory system crosses over at numerous points, effective auditory dysfunction treatment may require bilateral stimulation. Stimulation of the predetermined site is performed to modulate neuronal pathways of the auditory system. Modulation of this neuronal tissue may result in efficacious treatment of auditory dysfunction in a subject. While optimal results from the treatment may result in a complete resolution of the auditory dysfunction in a subject, any lessening of the amplitude of a subject's tinnitus may be considered successful according to the present invention.

One example of stimulation parameters used to treat auditory dysfunctions such as, for example, tinnitus, uses an amplitude in the range of about 2 mA to about 100 mA, a frequency in the range of about 3 Hz to about 50 Hz, and a pulse width in the range of about 5 microseconds to about 100 microseconds. As noted above, this is an exemplary set of stimulation parameters. Embodiments of the invention contemplate adjusting stimulation parameters to optimize treatment for each individual, and the stimulation parameters accordingly vary depending on the auditory dysfunction, and a multitude of other factors.

One of skill in the art is aware that stimulation parameters can be varied to achieve the desired result. One such parameter that may be varied in the present invention is signal frequency. Altering the frequency signal can result in the generation of a bursting type rhythm or burst stimulus frequency or burst mode stimulation, as Burst mode stimulation may also be used as described above and in U.S. application "New Stimulation Design for Neuromodulation", filed Oct. 20, 2005 incorporated by reference herein.

In certain embodiments, the burst stimulus frequency may be in the range of about 1 Hz to about 100 Hz, more particular, in the range of about 1 Hz to about 12 Hz, and more particularly, in the range of about 1 Hz to about 4 Hz, 4 Hz to about 7 Hz or about 8 Hz to about 12 Hz for each burst. One skilled in the art will further realize that each burst stimulus comprises at least two spikes, for example, each burst stimulus can comprise about 12 to about 100 spikes, more particularly, about 2 to about 10 spikes. Each spike can comprise a frequency in the range of about 50 Hz to about 1000 Hz, more particularly, in the range of about 200 Hz to about 500 Hz. One of skill in the art is aware that the frequency for each spike within a burst can be variable, thus it is not necessary for each spike to contain similar frequencies, e.g., the frequencies can vary in each spike. The inter-spike interval can be also vary, for example, the inter-spike interval, can be about 0.5 milliseconds to about 100 milliseconds or any range therebetween. The burst stimulus is followed by an inter-burst interval a duration in the range of about 5 milliseconds to about 5 seconds, more preferably, about 10 milliseconds to about 300 milliseconds. It is envisioned that the burst stimulus has a duration in the range of about 10 milliseconds to about 5 seconds, more particular, in the range of about 250 msec to 1000 msec (1-4 Hz burst firing), 145 msec to about 250 msec (4-7 Hz,), 145 msec to about 80 msec (8-12 Hz) or 1 to 5 seconds in plateau potential firing. The burst stimulus and the inter-burst interval can have a regular pattern or an irregular pattern (e.g., random or irregular harmonics).

In the auditory system, tonic firing transmits the contents of auditory information, while burst firing transmits the change in the incoming signal which may include the valence or importance attached to that sound (Lisman 1997; Sherman 2001; Swadlow and Gusev 2001). Repetitive stimulus presentation results in decreased neuronal response to that stimulus, known as auditory habituation at the single cell level (Ulanovsky et al., 2003), auditory mismatch negativity at multiple cell level (Naatanen et al., 1993; Ulanovsky et al., 2003).

Many auditory dysfunctions are constantly present. For example, tinnitus is usually constantly present, e.g., a non-rational valence is attached to the internally generated sound, and there is no auditory habituation to this specific sound, at this specific frequency. Thus, tinnitus is the result of hyperactivity of lesion-edge frequencies, and auditory mismatch negativity in tinnitus patients is specific for frequencies located at the audiometrically normal lesion edge (Weisz 2004).

As pathological valence of the tinnitus sound is mediated by burst firing, burst firing is increased in tinnitus in the extralemniscal system (Chen and Jastreboff 1995; Eggermont and Kenmochi 1998; Eggermont 2003), in the inner hair cells (Puel 1995; Puel et al., 2002), the auditory nerve (Moller 1984), the dorsal and external inferior colliculus (Chen and Jastreboff 1995), the thalamus (Jeanmonod, Magnin et al., 1996) and the secondary auditory cortex (Eggermont and Kenmochi 1998; Eggermont 2003). Furthermore, quinine, known to generate tinnitus, induces an increased regularity in burst firing, at the level of the auditory cortex, inferior colliculus and frontal cortex (Gopal and Gross 2004). It is contemplated that tinnitus can only become conscious if an increased tonic firing rate is present in the lemniscal system, generating the sound. This increased firing activity has been demonstrated in the lemniscal dorsal cochlear nucleus (Kaltenbach, Godfrey et al., 1998; Zhang and Kaltenbach 1998; Kaltenbach and Afman 2000; Brozoski, Bauer et al., 2002;

Zacharek et al., 2002; Kaltenbach et al., 2004), inferior colliculus (Jastreboff and Sasaki 1986; Jastreboff, Brennan et al., 1988; Jastreboff 1990) (Gerken 1996) and primary auditory cortex (Komiya, 2000). Interestingly, not only tonic firing is increased generating the tinnitus sound, but also burst firing (Ochi and Eggermont 1997) (keeping it conscious) at a regular basis. Repetitive burst firing is known to generate tonic gamma band activity (Gray and Singer 1989; Brumberg, 2000). Thus, it is envisioned that certain embodiments of the present invention can be used to modify burst firing, thus modifying tonic gamma activity. However, other pathways may be employed by embodiments of the invention that potentially contribute to the treatment efficacy.

Burst mode firing boosts the gain of neural signaling of important or novel events by enhancing transmitter release and enhancing dendritic depolarization, thereby increasing synaptic potentiation. Conversely, single spiking mode may be used to dampen neuronal signaling and may be associated with habituation to unimportant events (Cooper 2002). It is believed that the main problem in tinnitus is that the internally generated stimulus does not decay due to the presence of regular bursting activity telling the cortex this signal is important and has to remain conscious.

Thus, in the present invention, it is envisioned that a burst mode type stimulation can attack either of these two pathways: slowing down tonic firing in the lemniscal system (below 40 Hz) or removing the valence attached to it by the extralemniscal system by suppressing the regular bursting rhythm, thereby treating auditory dysfunctions such as tinnitus. Yet further, the system of the present invention can also make the auditory dysfunction disappear via auditory habituation. Suppressing the rhythmic burst firing in the frontal cortex may alter the emotional effect of tinnitus, with the tinnitus persisting, but without much influence on the daily life of a tinnitus sufferer. This auditory habituation or emotional effect can be produced by stimulating the amygdala and producing a corresponding effect on the linking pathways from the amygdala to the brain's memory systems described above. For example, stimulation of the amygdala may moderate auditory information passing via the amygdala to the hippocampus, causing auditory dysfunctions such as tinnitus to be essentially ignored or ignorable by the patient.

Using the therapeutic stimulation system of the present invention, the predetermined site is stimulated in an effective amount or effective treatment regimen to decrease, reduce, modulate or abrogate the auditory dysfunction. Thus, a subject is administered a therapeutically effective stimulation so that the subject has an improvement in the parameters relating to the dysfunction, such as, for example, the Goebel tinnitus questionnaire or other validated tinnitus questionnaires, audiometry, tinnitus matching, impedence, BAEP, and OAE. The improvement is any observable or measurable improvement. Thus, one of skill in the art realizes that a treatment may improve the patient condition, but may not be a complete cure of the disease.

Still further, since single presynaptic spikes that occur at low frequency and are properly timed to the troughs of theta may be a relevant mechanism for decreasing the strength of potentiated synapses (Huerta and Lisman 1996). In other words, if left amygdala activity is increased, as in tinnitus (Shulman 1995; Shulman, Strashun et al. 1995; Lockwood, Salvi et al. 1998; Moller 2003; Wallhausser-Franke, Mahlke et al. 2003; Mahlke and Wallhausser-Franke 2004) and phantom pain (Porro 2003; Lehner, Taracha et al. 2004; Lu, Wu et al. 2004) theta stimulation of the amygdala might be able to suppress tinnitus and phantom pain.

It is known that tinnitus is a result of a decreased habituation of the lesion edge frequencies after partial auditory deafferentation (Weisz, Voss et al. 2004). Since habituation reflects focusing of attention to relevant features of stimuli, impairment of this mechanism and subsequent defective memory trace formation may contribute to the tinnitus sound to be considered relevant constantly. Recently the human amygdala has been considered as a 'relevance detector' integrating the classical 'fear module' hypothesis with the concept of an evolved neural system devoted to the processing of a broader category of biologically relevant stimuli (especially social stimuli) (Sander, Grafman et al. 2003). Thus, it is envisioned that a decrease in amygdala activity via theta stimulation can result in the internally generated auditory stimulus (tinnitus) or internally generated sensory stimulus (pain) becoming less relevant and thus less perceived. In other words, amygdala theta stimulation is capable of suppressing tinnitus and pain.

B. Affective Disorders

Accordingly, the present invention relates to modulation of neuronal activity to affect psychological or psychiatric activity and/or mental activity. The present invention finds particular application in the modulation of neuronal function or processing to effect a functional outcome. The modulation of neuronal function is particularly useful with regard to the prevention, treatment, or amelioration of psychiatric, psychological, conscious state, behavioral, mood, and thought activity (unless otherwise indicated these will be collectively referred to herein as "psychological activity" or "psychiatric activity" or "mental activity"). When referring to a pathological or undesirable condition associated with the activity, reference may be made to "psychiatric disorder" or "psychological disorder" instead of psychiatric or psychological activity. Although the activity to be modulated usually manifests itself in the form of a disorder such as a mood disorder (i.e., major depressive disorder, bipolar disorder, and dysthymic disorder) or an anxiety disorder (i.e., panic disorder, posttraumatic stress disorder, obsessive-compulsive disorder and phobic disorder), it is to be appreciated that the invention may also find application in conjunction with enhancing or diminishing any neurological or psychiatric function, not just an abnormality or disorder. Psychiatric activity that may be modulated can include, but not be limited to, normal functions such as alertness, conscious state, drive, fear, anger, anxiety, euphoria, sadness, and the fight or flight response.

Using the therapeutic stimulation system of the present invention, the predetermined site or target area is stimulated in an effective amount or effective treatment regimen to decrease, reduce, modulate or abrogate the mood and/or anxiety disorder. Thus, a subject is administered a therapeutically effective stimulation so that the subject has an improvement in the parameters relating to the affective disorder including subjective measures such as, for example, neurological examinations and neuropsychological tests (i.e., Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, MADRAS, CGI, N-BAC, or Yale-Brown Obsessive Compulsive score (Y-BOCS)), motor examination, and cranial nerve examination, and objective measures including use of additional psychiatric medications, such as anti-depressants, or other alterations in cerebral blood flow or metabolism and/or neurochemistry. The improvement is any observable or measurable improvement. Thus, one of skill in the art realizes that a treatment may improve the patient condition, but may not be a complete cure of the disease.

1. Depression

In one embodiment of the invention, depression is treated using the stimulation system of the present invention.

Depression has been associated with alterations in a circuit of brain regions hypothesized to include the frontal cortex, hippocampus, amygdala, striatum, and thalamus (Bremner 2002). The amygdala, hippocampus, and pregenual anterior cingulate are potential targets for the neurosurgical treatment of depression (Rauch 2003).

Similarly to the sensory systems, the emotional system consists of a ventral and dorsal stream 1) a ventral system, including the amygdala, insula, ventral striatum, ventral anterior cingulate gyms, and prefrontal cortex, for identification of the emotional significance of a stimulus, production of affective states, and automatic regulation of emotional responses; and 2) a dorsal system, including the hippocampus, dorsal anterior cingulate gyms, and prefrontal cortex, for the effortful regulation of affective states and subsequent behavior (Phillips, Drevets et al. 2003; Phillips, Drevets et al. 2003).

Cognitive and neurophysiological studies have shown that hippocampal-prefrontal processing is impaired in depression, and amygdaloid processing is enhanced (Diamond, Campbell et al. 2004).

Evidence is increasing that amygdala and hippocampus also show significant structural abnormalities in affective disorders. Compared with control subjects, depressive subjects have significantly larger (+13%) amygdala volumes and significantly smaller (−12%) hippocampal volumes. Furthermore an inverse correlation between the length of illness and left hippocampus volumes and right superior temporal gyms volumes has been demonstrated (Caetano, Hatch et al. 2004).

Hippocampal volume is reduced in patients with unipolar depression, maybe as a consequence of repeated periods of major depressive disorder (Videbech and Ravnkilde 2004). The reduction in gray matter volume and the morphological atrophy are probably due to an excess of neural loss (apoptosis) and an altered regulation of the neurotrophic processes. Hence, a deficit in neurotrophic factor synthesis (brain-derived neurotrophic factor, neurotrophin-3, NT-4/5, Bcl-2, etc.) may be responsible for increased apoptosis in the hippocampus and prefrontal cortex corresponding to the cognitive impairment described in depression. This hypothesis seems to be confirmed by the decreased expression of neurotrophic factors (e.g., BDNF mRNA) in animal models of depression. In parallel, the neural plasticity (functional aspects of synaptic connectivity and long-term potential activity) is decreased. However, the most interesting data concern the possible reversibility of this dysregulation with antidepressant treatment. For example, communication between the hippocampus and the prefrontal cortex could be re-established, enabling in a way the cognitive processes to be "reset." (Fossati, Radtchenko et al. 2004).

Still further, it is known that the size of the amygdala is enlarged in the first years of the disorder, and may decrease with prolonged disorder duration (Lange and Irle 2004). Thus, the present invention uses theta stimulation of the amygdala amygdalohippocampal complex or projections associated therewith to treat depression.

2. Bipolar Disorder

Bipolar disorder is a major public health problem, with estimates of lifetime prevalence in the general population of the United States ranging from 1 to 1.6 percent (Robins and Regier 1991) and from 0.3 to 1.5 percent worldwide (Weissman, Bland et al. 1996; Hilty, Brady et al. 1999). Over the course of a lifetime, bipolar I disorder affects approximately 0.8 percent of the adult population, and bipolar II disorder affects approximately 0.5 percent (Weissman, Bruce et al. 1990). Bipolar disorder is also associated with significant mortality risk; approximately 25 percent of patients attempt suicide at some time during their lives, and 11 percent of patients die by suicide (Hilty, Brady et al. 1999).

Functional studies have found that the activity of the dorsal prefrontal cortex and the anterior cingulate are closely associated with mood symptoms. Activity in the ventral and orbital prefrontal cortex appears reduced both during episodes and in remission. In contrast, amygdala activity shows a persistent increase. This might lead to a excitotoxicity with decrease in amygdalar volume (DelBello, Zimmerman et al. 2004). It is suggested that abnormal interaction between the amygdala and the ventral/orbitofrontal cortex may be a central feature of the pathophysiology of bipolar disorder (Haldane and Frangou 2004). In bipolar disorder, there may be diminished prefrontal modulation of subcortical and medial temporal structures within the anterior limbic network (eg, amygdala, anterior striatum and thalamus) resulting in dysregulation of mood.

Bipolar patients did not seem to show a reduction in hippocampal volume (Videbech and Ravnkilde 2004)

Functionally distinct prefrontal cortices receive projections from different components of the hippocampal region. Projection of neurons from the hippocampal formation innervate predominantly the medial frontal cortex and to a lesser degree the orbital prefrontal areas (Barbas and Blatt 1995), the opposite from what is known for the amygdala (Barbas and De Olmos 1990).

Single presynaptic spikes that occur at low frequency and are properly timed to the troughs of theta may be a relevant mechanism for decreasing the strength of potentiated synapses (Huerta and Lisman 1996). In other words if left amygdala activity is increased, as in depression (Drevets, Bogers et al. 2002) theta stimulation should be able to reduce left amygdala activity. A decrease in amygdalar metabolism has been demonstrated to correlate with clinical improvement in depressed patients (Drevets, Bogers et al. 2002).

In view of the above, it is contemplated that bi-polar disorder might be treated by theta stimulation of the amygdala.

3. Other Affective Disorders

In addition to depression, it is envisioned that the stimulation system of the present invention can be used to treat other affective disorders, such as posttraumatic stress disorder (PTSD), psychological trauma, anxiety, obsessive compulsive disease.

A posttraumatic stress disorder is an internal cognitive stimulus that keeps on getting attention, even if it is unnecessary. The present invention contemplates stimulating the amygdalohippocampal complex to reset it, thus removing the relevance of this stimulus (by pacing it down).

Still further, the present invention can be used to treat obsessive compulsive disorder (OCD). Stimulation of the amygdalohippocampal complex and reset it, and thereby stopping the priority mode and the obsessive behavior will stop.

VI. Example

The following example is included to demonstrate preferred embodiments of the invention. It should be appreciated by those of skill in the art that the techniques disclosed in the example which follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE

Treatment of Tinnitus

Five patients with unilateral tinnitus were treated with an amytal test of the anterior choroidal artery to determine if the AHC is involved in the patients' disorder. Standard procedures are used to perform an amytal test on the patients.

Briefly, 80 mg amobarbital was injected on one side of the body and the patient's tinnitus was evaluated. The AHC on the other hemisphere was treated after the effects of the amobarbital subside, usually after about 10 minutes.

Tinnitus was evaluated using TMS, TENS, the Goebel tinnitus questionnaire, audiometry, tinnitus matching, impedance, BAEP, and OAE. Patients that see 60 percent or more reduction in the tinnitus symptoms are then evaluated for introduction of an AHC electrode to be implanted in the position indicated in FIG. 3. In this study, 3 of 5 patients saw greater than 60% suppression of tinnitus during the contralateral amytal test. Results from the study are shown in the table in FIG. 5.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference.

U.S. Pat. No. 5,496,369
U.S. Pat. No. 5,697,975
U.S. Pat. No. 5,713,847
U.S. Pat. No. 5,735,885
U.S. Pat. No. 5,788,656
U.S. Pat. No. 6,210,321
U.S. Pat. No. 6,456,886
U.S. Pat. No. 6,656,172
Barbas, H. and G. J. Blatt (1995). Hippocampus 5(6): 511-33.
Barbas, H. and J. De Olmos (1990). J Comp Neurol 300(4): 549-71.
Benabid, et al. (2005). C R Biol 328(2): 177-86.
Benarroch, E. E. (1993). Mayo Clin Proc 68(10): 988-1001.
Bremner, J. D. (2002). CNS Spectr 7(2): 129-30.
Caetano, S. C., J. P. Hatch, et al. (2004). Psychiatry Res 132(2): 141-147.
Cook, C. J. (2004). Physiol Behav 82(4): 751-62.
Cummings, J. and M. Mega (2003). Neuropsychiatry and behavioral neuroscience. Oxford, Oxford Universiy Press.
De Souza, E. B. (1995). Psychoneuroendocrinology 20(8): 789-819.
DelBello, M. P., M. E. Zimmerman, et al. (2004). Bipolar Disord 6(1): 43-52.
Diamond, D. M., A. Campbell, et al. (2004). Eur Neuropsychopharmacol 14(Suppl 5): S491-S495.
Drevets, W. C., W. Bogers, et al. (2002). Eur Neuropsychopharmacol 12(6): 527-44.
Feldman, S., R. A. Siegel, et al. (1983). Neuroscience 9(1): 157-63.
Fossati, P., A. Radtchenko, et al. (2004). Eur Neuropsychopharmacol 14 Suppl 5: S503-10.
Foxe et al., Cognitive Brain Research 10:77-83 (2000)
Fu et al., The Journal of Neuroscience 23(20):7510-7515 (2003)
Haldane, M. and S. Frangou (2004). Prog Neuropsychopharmacol Biol Psychiatry 28(6): 943-60.
Hilty, D. M., K. T. Brady, et al. (1999). Psychiatr Serv 50(2): 201-13.
Huerta, P. T. and J. E. Lisman (1996). J Neurophysiol 75(2): 877-84.
International Pub. No. WO 01/08617
Jones, Trends in Neuroscience, Vol. 24, No. 10:595-601 (2001)
Jurkowski, M., W. Trojniar, et al. (2001). Brain Behav Immun 15(1): 93-113.
Lange, C. and E. Irle (2004). Psychol Med 34(6): 1059-64.
Lehner, M., E. Taracha, et al. (2004). Neurosci Lett 370(1): 74-9.
Lockwood, A. H., R. J. Salvi, et al. (1998). Neurology 50(1): 114-20.
Lu, C. L., Y. T. Wu, et al. (2004). Neurogastroenterol Motil 16(5): 575-87.
Mahlke, C. and E. Wallhausser-Franke (2004). Hear Res 195 (1-2): 17-34.
Mirz et al., Hearing Research 134:133-144 (1999)
Moller and Rollins, Neuroscience Letters 319:41-44 (2002)
Moller et al., Laryngoscope 102:1165-1171 (1992)
Moller, A. R. (2003). Otolaryngol Clin North Am 36(2): 249-66, v-vi.
Norton, BioMedical Engineering OnLine 2:6 (2003)
Petrov, T., J. H. Jhamandas, et al. (1996). Cell Tissue Res 283(3): 367-74.
Phillips, M. L., W. C. Drevets, et al. (2003). Biol Psychiatry 54(5): 504-14.
Porro, C. A. (2003). Neuroscientist 9(5): 354-69.
Rauch, S. L. (2003). Neurosurg Clin N Am 14(2): 213-23, vii-viii.
Robins, L. and D. Regier, Eds. (1991). Psychiatric Disorders in America: The Epidemiologic Catchment Area Study. New York, Free Press.
Roozendaal, B., J. M. Koolhaas, et al. (1991). Physiol Behav 50(4): 777-81.
Sander, D., J. Grafman, et al. (2003). Rev Neurosci 14(4): 303-16.
Shulman, A. (1995). Int Tinnitus J 1(2): 115-126.
Shulman, A., A. M. Strashun, et al. (1995). Int Tinnitus J 1(1): 13-29.
Tardif et al., Neuroscience 116:1111-1121 (2003)
Velasco et al., (2001) J. Clinical Neurophysiology 18(6):495-513.
Videbech, P. and B. Ravnkilde (2004). Am J Psychiatry 161 (11): 1957-66.
Vonck et al., (2002). Ann Neurol 52:556-565.
Vonck et al., (2005) Epilepsia 46(Suppl. 5):98-99.
Wallhausser-Franke et al., Experimental Brain Research 153: 649-654 (2003)
Wallhausser-Franke, E., C. Mahlke, et al. (2003). Exp Brain Res 153(4): 649-54.
Weissman, M. M., R. C. Bland, et al. (1996). Jama 276(4): 293-9.
Weissman, M., M. Bruce, et al. (1990). Affective disorders, in Psychiatric Disorders in America. L. Robins and D. Regier. New York, Free Press.
Weisz, N., S. Voss, et al. (2004). BMC Neurosci 5(1): 8.
Zhang et al., Experimental Brain Research 153:655-660 (2003)

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of alleviating post traumatic stress disorder (PTSD) in a patient comprising:
    identifying PTSD in the patient;
    positioning at least an electrical lead within the patient such that at least one electrode of the electrical lead is disposed within or in direct contact with a central nucleus of amygdala brain tissue of the patient;
    selecting a plurality of operating parameters for an electrical stimulation system that are effective for treating PTSD;
    programming the electrical stimulation system according to the plurality of operating parameters;
    activating the electrical stimulation system to deliver electrical pulses to the electrode within or in direct contact with the central nucleus; and
    determining whether the electrical pulses have caused alleviation in symptoms of PTSD.

2. The method of claim 1 further comprising generating, by the IPG, a burst stimulus that comprises a plurality of groups of spike pulses, wherein the burst stimulus is substantially quiescent between the plurality of groups, wherein each spike within each group is separated by a maximum inter-spike interval and each group of spikes is separated by a minimum inter-group interval, wherein the maximum inter-spike interval is 5 milliseconds and the minimum inter-group interval is 20 milliseconds.

3. A method of treating an anxiety disorder in a patient comprising
    identifying the anxiety disorder in the patient;
    positioning at least an electrical lead within the patient such that at least one electrode of the electrical lead is disposed within or in direct contact with a central nucleus of amygdala brain tissue of the patient;
    selecting a plurality of operating parameters for an electrical stimulation system that are effective for treating the anxiety disorder;
    programming the electrical stimulation system according to the plurality of operating parameters;
    activating the electrical stimulation system to deliver electrical pulses to the electrode within or in direct contact with the central nucleus; and
    determining whether the electrical pulses have resulted in effective treatment of the anxiety disorder of the patient.

4. The method of claim 3 wherein the anxiety disorder is selected from the group consisting of post-traumatic stress disorder, panic disorder, obsessive-compulsive disorder, and phobias.

5. The method of claim 4 wherein the anxiety disorder is the post-traumatic stress disorder.

6. The method of claim 3 further comprising generating, by the stimulation system, a burst stimulus that comprises a plurality of groups of spike pulses, wherein the burst stimulus is substantially quiescent between the plurality of groups, wherein each spike within each group is separated by a maximum inter-spike interval and each group of spikes is separated by a minimum inter-group interval, wherein the maximum inter-spike interval is 5 milliseconds and the minimum inter-group interval is 20 milliseconds.

* * * * *